United States Patent
Blumenfeld et al.

(10) Patent No.: US 6,369,038 B1
(45) Date of Patent: *Apr. 9, 2002

(54) CLOSED ANTISENSE AND SENSE OLIGONUCLEOTIDES AND THEIR APPLICATIONS

(75) Inventors: Marta Blumenfeld, Paris; Pascal Brandys, Suresnes; Luc d'Auriol; Marc Vasseur, both of Paris, all of (FR)

(73) Assignee: Genset (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/137,134

(22) PCT Filed: Apr. 24, 1992

(86) PCT No.: PCT/FR92/00370

§ 371 Date: Nov. 23, 1993

§ 102(e) Date: Nov. 23, 1993

(87) PCT Pub. No.: WO92/19732

PCT Pub. Date: Nov. 12, 1992

(30) Foreign Application Priority Data

Apr. 25, 1991 (FR) .............................. 91 05114

(51) Int. Cl.⁷ ................................. C12Q 1/68
(52) U.S. Cl. .......................... 514/44; 435/6; 435/91.1; 536/23.1
(58) Field of Search ................... 435/91.1, 6; 536/23.1, 536/24.2, 24.3, 24.31; 514/44, 2

(56) References Cited

U.S. PATENT DOCUMENTS

| | | | | |
|---|---|---|---|---|
| 5,405,775 A | * | 4/1995 | Inouye et al. ........... | 435/252.33 |
| 5,426,180 A | | 6/1995 | Kool ....................... | 536/25.3 |
| 5,434,070 A | * | 7/1995 | Inouye et al. ............ | 435/194 |
| 5,436,141 A | * | 7/1995 | Miyata et al. ............. | 435/91.1 |
| 5,683,985 A | | 11/1997 | Chu et al. ................ | 514/44 |

FOREIGN PATENT DOCUMENTS

| | | |
|---|---|---|
| DE | 3928900 | 3/1991 |
| EP | 0321201 | 6/1989 |

OTHER PUBLICATIONS

USB Molecular Biology Reagents/Protocols 1992, Published by the United States Biochemical Corporation, Cleveland, Ohio, 1991, p. 618.*

D.A. Erie et al., "Melting behavior of a covalently closed, single stranded, circular DNA", Biochemistry, vol. 28, No. 1, Jan. 10, 1989, pp. 268–273.

T. Yagura et al., "Mechanism of stimulation by a specific protein factor of de novo DNA synthesis by mouse DNA . . . ", Nucleic Acids Research, vol. 11, No. 18, Sep. 24, 1983, pp. 6369–6380.

N.N.L. Shen et al., "Introduction of single–stranded ADH genes into Drosophilia results in tissue–specific expression", Biochem. & Biophys. Res. Comm., vol. 174, No. 3, Feb. 14, 1991, pp. 1300–1305.

Y. Okada, "Viroid, a replicating single–stranded circular RNA", Chem. Abs., vol. 101, No. 17, Oct. 22, 1984, p. 149, Col. 1, Abs. No. 144891t.

D. Mattanovich et al., "Stopping the DNA polymerase activity at a specific site with a dideoxyoligonucleotide: selective labelling . . . ", Nucleic Acids Res., vol. 17, No. 20, Oct. 25, 1989, p. 8384.

Blumenfeld et al, J. Cellular Biochemistry, Suppl. 15D, Feb. 2–Mar. 1, 1991, Abstract No. CD 202.*

* cited by examiner

*Primary Examiner*—James Martinell
(74) *Attorney, Agent, or Firm*—Saliwanchik, Lloyd & Saliwanchik

(57) ABSTRACT

An antisense or sense agent of the oligonucleotide type, includes a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed, single-stranded branched structure.

91 Claims, 13 Drawing Sheets

CLOSED ANTISENSE AND SENSE OLIGONUCLEOTIDES AND THEIR APPLICATIONS

The present invention relates to compounds of the oligonucleotide type, as well as to their applications.

Antisense oligonucleotides are short synthetic DNA or RNA molecules of sequence complementary to a target sequence belonging to a gene or to a messenger RNA whose expression it is desired to block specifically. Antisense oligonucleotides may be directed towards a messenger RNA sequence, or alternatively towards a DNA sequence. Antisense oligonucleotides hybridize with the sequence to which they are complementary and can thus block the expression of the messenger RNA carrying this sequence.

The term "oligonucleotide" is used in a general manner to denote a polynucleotide of ribo- or deoxyribo-series. Where the issue of a particular property linked to the use of a deoxyribo-series or a ribo-series is involved, the complete name oligodeoxyribonucleotide or oligoribonucleotide may be used. An oligonucleotide can be single-stranded, that is to say contain only one line of nucleotides which are not paired with another chain, or can alternatively be double-stranded, that is to say contain nucleotides paired with another polynucleotide chain. Two complementary oligonucleotides form a double-stranded structure. A single-stranded oligonucleotide can, however, possess double-stranded regions by intra-chain pairings between complementary sequences carried on the same strand.

The term hybridization used here means the formation of hydrogen bonds between pairs of complementary bases, guanine and cytosine forming three hydrogen bonds and adenine and thymine forming two.

Antisense oligonucleotides are synthesized chemically, and frequently contain modifications which change the actual skeleton of the molecule or carry additional reactive groups localized at their ends. The objectives of these modifications introduced into anti-sense oligonucleotides are either to enhance the resistance of these molecules to nucleolytic degradation, or to promote their interactions with their targets, or to permit specific degradation/modification reactions of the RNA or DNA targets, or to increase their intracellular penetration.

Antisense oligonucleotides are sensitive to nuclease degradation, and mainly to the action of exonucleases. Nucleases occur in all compartments—cellular and extracellular, especially in the serum—and cause a rapid degradation of these molecules. A pharmacological use of antisense molecules involves solving these problems of degradation in order to achieve satisfactory pharmacokinetics and hence an adequate perpetuation of the effects of these molecules. Many chemical modifications enable antisense oligonucleotides to become nuclease-resistant. Some modifications directly affect the structure or nature of the phosphodiester bond (methylphosphonates, phosphorothioates, alpha-oligonucleotides, phosphoramidates, to mention a few examples), other [sic] consist in adding blocking groups to the 3' and 5' ends of the molecules (Perbost et al., 1989; Bertrand et al., 1989; Bazile et al., 1989; Andrus et al., 1989; Cazenave et al., 1989; Zon, 1988; Maher and Dolnick, 1988; Gagnor et al., 1987; Markus-Sekura, 1987).

To increase the efficacy of the interactions between an oligonucleotide and its target, an inter-calating group (acridines for example) may be added to one end of the antisense oligonucleotide. Lastly, re-active groups (alkylating agents, psoralens, Fe-EDTA for example) capable of causing cleavages or permanent chemical changes in the target may be added to the antisense oligonucleotides (Sun et al., 1989; Helene, 1989; Durand et al., 1989; Sun et al., 1988; Helene and Thuong, 1988; Verspieren et al., 1987; Sun et al., 1987; Cazenave et al., 1988, 1987; Le Doan et al., 1987; Toulme et al., 1986; Vlassov et al., 1986).

The last type of conventional modification of antisense oligonucleotides consists in adding groups which modify the charge and/or hydrophilicity of the molecules in order to facilitate their passage through the membrane (Kabanov et al., 1990; Degols et al., 1989; Stevenson et al., 1989; Leonetti et al., 1988).

All these modifications can obviously be combined with one another.

Not all the regions of a messenger RNA are sensitive in a like manner to the effects of an antisense oligonucleotide. A messenger RNA is not a set linear molecule but, on the contrary, a molecule possessing many secondary structural features (complex intramolecular hybridizations) and tertiary structural features (refoldings and particular conformations, pseudo-nodes), and which interacts with structural and functional nucleo-proteins (basic proteins, splicing, polyadenylation and capping complexes, translation complex for example). The effective availability and accessibility of the different regions of a messenger RNA will depend on their engagement in these structural features. Correspondingly, the efficacy of an inhibitory agent which interacts with this or that sequence will also depend on the engagement of this sequences [sic] in a particular function. The target regions for antisense molecules must be accessible to the oligonucleotide.

The use of software for prediction of secondary structures enables theoretical degrees of accessibility to be predicted, and hence the choice of targets for antisense oligonucleotides to be guided. As a whole, the regions most widely used as targets are translation initiation sites (AUG initiation region) and also splicing sites (SD/SA junctions). Many other sequences not having particular functional properties and not engaged in intramolecular pairing have also proved effective as a target for antisense oligonucleotides (see the examples mentioned later).

Antisense oligodeoxyribonucleotides may also be directed towards certain regions of double-stranded DNA (homopurine/homopyrimidine sequences or purine/pyrimidine-rich sequences), and can thus form triple helices (Perroualt et al., 1990; François et al.(A), 1989; François et al.(B), 1989; François et al.(C), 1989; Wang et al., 1989; Maher et al., 1989; Sun et al., 1989; Boidot-Forget et al., 1988; Moser and Dervan, 1987; Dervan, 1986). Oligonucleotides directed in this manner towards DNA have been termed "anti-gene" or alternatively "anti-code". The formation of a triple helix at a particular sequence can block the binding of proteins involved in the expression of a gene and/or permit the introduction of irreversible damage into the DNA if the oligonucleotide in question possesses a particular reactive group. Such antisense oligonucleotides can become true artificial restriction endonucleases, directed on request towards specific sequences.

The hybridization between an antisense oligonucleotide and a target messenger RNA can block expression of the latter in several ways, either sterically or pseudocatalytically (Gagnor et al., 1989; Jesus et al., 1988; Markus-Sekura, 1987):

the interaction between the messenger RNA and a complementary antisense oligonucleotide can create a physical barrier preventing the binding and/or progression of proteins or protein complexes needed for translation, maturation, stabilization or transport of the messenger RNA. This physical blockade will lead finally to an inhibition of the expression of the target messenger RNA.

the hybridization between a messenger RNA and an antisense oligodeoxyribonucleotide will create a substrate for RNase H, an enzyme present in all eukaryotic cells. RNase H is an enzyme which specifically degrades RNA when it is hybridized with DNA. The hybridization of an antisense oligonucleotide with a target RNA will hence lead to cleavage of this target RNA at the location of this hybridization, and hence to its permanent inactivation.

moreover, as stated above, antisense oligonucleotides can contain reactive groups capable of directly producing irreversible damage in the target RNA molecule.

As regards antisense oligonucleotides directed towards DNA, these can act either by inhibiting the binding of a regulatory protein essential to expression of the target gene (transcription factor for example), or by producing irreversible damage (cleavages, cross-links) in the DNA molecule, making it locally incapable of genetic expression.

Ribozymes are RNA molecules endowed with enzymatic activity, capable, in particular, of causing endonuclease cleavages in target RNAs. A ribozyme may be considered to be a particular antisense oligonucleotide endowed with a natural endonuclease catalytic activity (Vasseur, 1990; Symons, 1989; Jeffrie and Symons, 1989; Haseloff and Gerlach, 1988; Uhlenbeck, 1987; Symons et al., 1987). Typically, a ribozyme consists of two portions; on the one hand it contains a sequence complementary to the target sequence which it is desired to cut, and on the other hand a catalytic sequence functioning as a reactive group (Fedor and Uhlenbeck, 1990; Uhlenbeck et al., 1989; Sheldon and Symons, 1989; Sampson et al., 1987). It is possible at the present time, using a consensus active site deduced from the sequence of viral ribozymes, to cut theoretically any messenger RNA at a predetermined position (Haseloff and Gerlach, 1988; Uhlenbeck, 1987). Ribozymes encounter the same problems of use as conventional antisense oligonucleotides, especially as regards the phenomena of degradation, RNAs being still more sensitive to nucleolytic degradation than DNAS.

Antisense oligonucleotides make it possible to block specifically the expression of cell messenger RNAs, for example oncogenic type messengers (Tortora et al., 1990; Chang et al., 1989; Anfossi et al., 1989; Zheng et al., 1989; Shuttleworth et al., 1988; Cope and Wille, 1989; Cazenave et al., 1989) and many different types of viral messenger RNAs originating from viruses as varied as VSV (Degols et al., 1989; Leonetti et al., 1989), SV40 (Westermann, et al., 1989), influenza viruses (Kabanov et al., 1990; Zerial et al., 1987), the encephalomyocarditis virus (Sankar et al., 1989), adenovirus (Miroschnichenko et al., 1989), HSV (Gao et al., 1988) and HIV (Matzukura et al., 1989; Stevenson et al., 1989; Matzukura et al., 1988; Goodchild et al., 1988).

With ribozymes, it is possible to cleave in vivo the messenger RNA coding for the CAT marker gene (Cameron and Jennings, 1989), to inhibit the process of maturation of histone messenger RNA (Cotten et al. 1989; Cotten and Birnstiel, 1989) or to protect the cell partially against HIV-1 infection (Sarver et al., 1990).

Oligonucleotides may also be used in the context of "sense" type strategies. This approach consists in using a single-stranded or double-stranded oligonucleotide of the deoxyribo- or ribo-series, of specific sequence, as an agent for binding a protein possessing an affinity for this sequence and whose effective concentration inside the cells it is desired to decrease, by competition. It is thus possible to envisage using oligonucleotides which interact with transcription factors, viral encapsidation factors, translation regulation factors, and the like. This approach is not yet exploited, unlike the more conventional antisense strategy. In this case, the problem of the stability of the oligonucleotides is also a critical important factor for the efficacy and durability of their action. The use of modified oligonucleotides for such an approach can run into structural problems of recognition by the proteins. The possibility of having at one's disposal natural oligonucleotides which are stable in serum and cells would make it possible to envisage the development of novel therapeutic methods targeted especially on the regulation factors having affinity for nucleic acids.

Antisense, and sense, oligonucleotides are hence potent and highly specific potential pharmacological agents which make it possible to inhibit the expression messengers coding for products exerting pathogenic effects.

The therapeutic use of oligonucleotides runs, however, into several problems of a physiological type, especially that of the intracellular delivery of these molecules and that of their sensitivity to nucleolytic degradation. The use of modified derivatives enables the problem of nuclease sensitivity to be overcome, but introduces a further problem, that of the possible toxicity of the chemical modifications introduced into the molecule.

The use of modified antisense oligonucleotides creates, in effect, problems of a toxicological nature. While some of the modifications are said to be fairly neutral, most are not without potential toxicity.

Chemically modified antisense oligonucleotides can possess a toxicity at several level [sic], either directly through effects of the whole molecule, or indirectly via the effects of the degradation products. Nucleotides carrying chemical modifications and which are present in a cell at a high concentration can thus possess a toxicity—and more especially a genotoxicity—which is not insignificant from a pharmacological standpoint.

For example, many problems raised by the use of modified antisense oligonucleotides, especially non-sequence-specific antiviral effects, appear indeed to be due to the nature of some of the chemical modifications introduced into the antisense oligonucleotides to make them nuclease-resistant.

From a toxicological standpoint, it is hence obvious that, the less the natural structure of the oligonucleotide is modified, the lower the risk of being confronted by pharmacological problems. A natural DNA or RNA molecule, as well as its degradation products, creates little or no problem of toxicology and of pharmacokinetics, which is not the case with a modified structure capable of giving, after being metabolized, multifarious potentially toxic derivatives.

It would hence be advantageous to be able to have at one's disposal natural oligonucleotides containing only normal deoxy- or ribonucleotides linked to one another via a normal phosphodiester bond but possessing, however, a resistance to degradation.

The subject of the invention presented here is a novel structural type of antisense, or sense, oligonucleotide which is resistant to exonucleases without the involvement of stabilizing chemical modifications. The oligonucleotides forming the subject of the invention have the feature of possessing a closed structure which does not offer an end available to exonuclease degradation.

Such oligonucleotides may be used in their natural state but can, however, also contain modified nucleotides or reactive groups, or be physically combined with other molecules or macromolecules with the object of fortifying their efficacy of inhibition, their penetration, their affinity for their targets or their cellular or intracellular targeting, or for optimizing any other property.

II. DESCRIPTION OF THE INVENTION

In cells and, still more, in the body, in the blood circulation for example, natural antisense oligonucleotides are sensitive to nucleases. Nucleases are degradative enzymes capable of cutting the phosphodiester bonds of DNA or RNA, either by introducing internal cleavages in single- or double-stranded molecules, or by attacking these molecules from their ends. Enzymes which attack internally are termed endonucleases, and those which attack by the ends are termed exonucleases.

The stability of antisense oligonucleotides—and hence their efficacy—may be considerably enhanced by introducing various chemical modifications making them resistant to degradation, as described above.

It is established that exonucleases are the species which are the main cause of degradation of antisense oligonucleotides in serum and in the cell. More especially, it appears that exonucleases attacking at the 3'-OH end are implicated most particularly in this phenomenon.

Modifications made to the structure of the ends of antisense oligonucleotides can protect them, block exonuclease activity and confer an increased stabilization on the oligonucleotides.

The invention described here is based on the novel idea that closed oligonucleotides not possessing free ends will hence be, by definition, resistant to this type of degradation. Closed, for example circular, oligonucleotides do not afford a substrate which is accessible to 3' or 5' exonucleases, and are hence thereby stabilized.

More especially, the invention hence relates to an antisense or sense agent of the oligonucleotide type, which consists of one or more single-stranded oligonucleotide sequence(s) whose ends are linked to one another via covalent links to form at least partially a closed, single-stranded structure.

These agents are sometimes designated hereinafter closed oligonucleotides or circular oligonucleotides, inasmuch as this type of compound preferably possesses a majority of nucleotides relative to non-nucleotide structures.

The definition of the term oligonucleotide has been given above, and incorporates both the natural ribo- and deoxyribo-series, as well as the modifications of these bases which will be designated as a whole hereinafter unnatural and which have also been mentioned above.

The covalent link can be a non-nucleotide covalent structure of the protein, lipid or glycoside type and/or a mixed structure, as will be explained below. It is nevertheless preferable to use a nucleotide covalent structure, that is to say a phosphodiester bond.

The invention relates to closed, for example circular, oligonucleotides not having free ends, but composed of a succession of nucleotide bases bonded to one another via all types of bonds, and preferably via phosphodiester type bonds. These bases may be combined with one another via bonds such that the distance between these bases will be approximately 3 Å to 4 Å, which is the distance found in natural DNA or RNA molecules when the internucleotide bonds are provided by phosphodiester groups. The closed, for example circular, oligonucleotides will advantageously be composed of natural nucleotides preferably bonded to one another via unmodified phosphodiester bonds, but may also contain modified nucleotides and/or modified bonds which comply with the distances between bases and permit the helical axial rotations characteristic of nucleic acid conformations. The closed oligonucleotides will hence be advantageously composed of the bases A, T, G, C, or U, in their deoxy- or ribonucleotide forms. The closed oligonucleotides may hence be either oligodeoxyribonucleotides or oligoribo nucleotides or mixed molecules containing deoxyribonucleotides and ribonucleotides.

The invention hence comprises any closed, single-stranded DNA or RNA—or mixed DNA/RNA—molecule, circular or possessing a circular portion, obtained biologically, chemically or by methods combining the techniques of synthetic chemistry with those of biology and biochemistry, possessing a resistance to exonucleases greater than that of an oligonucleotide of the same sequence but completely linear, not possessing a closed structure.

Examples of closed oligonucleotides are shown in FIGS. 1A to 1C.

FIG. 1A shows examples of closed antisense oligonucleotide structure. FIG. 1B shows examples of closed sense oligonucleotide structure. FIG. 1C shows a mixed molecule capable of exerting a sense and antisense effect.

The number of single nucleotides making up the closed oligonucleotides can vary widely, in particular between 10 and 200, but, as a guide, this number will advantageously be between about twenty and about fifty nucleotides, depending on the closing structure (circular, lasso or balloon structure, structure made double-stranded, and the like—see the descriptions of the different structures later), the uses (anti-RNA antisense molecule, anti-DNA antisense molecule, anti-protein sense molecule), the type of oligonucleotide—deoxy- or ribonucleotide—(simple antisense or ribozyme antisense, and the like) and the targets in question (messenger RNA, premessenger RNA, particular secondary structure, and the like).

The closed oligonucleotides forming the subject of the present invention are preferably composed of a sequence of bases containing adenine (A), guanine (G), cytosine (C), thymine (T) and uracil (U), having the general formulae shown in FIG. 1D.

The closed oligonucleotides may also contain rare nucleotides (inosine, I, or rI for example) or modified nucleotides, either of the deoxyribo- or the ribo-series.

The closed oligonucleotides may contain nucleotides modified at the phosphodiester bond, for example according to the various formulae shown in FIG. 2. For example, the closed oligonucleotides may contain one or more of the well known groups which are phosphorothioates, methylphosphonates, phosphorodithioates, phosphoselenates, phosphoramidates and alkyl phosphotriesters. It should be noted, however, that the closed antisense oligonucleotides will preferably comprise natural nucleotides linked to one another via unmodified phosphodiester bonds.

The closed oligonucleotides may contain reactive nucleotides capable of establishing links with the sequence of the target molecule complementary to the oligonucleotide.

Thus, the closed oligonucleotides may carry reactive groups grafted onto the nucleotides, such as, for example, psoralen groups, or other bridging agents or intercalating agents capable of reacting with the sequence of the target molecule complementary to the oligonucleotide (see the various non-exhaustive examples shown in FIG. 2).

The closed antisense oligonucleotides may also include, among the nucleotides forming part of the closed structure, an RNA sequence possessing a catalytic activity. These circular oligonucleotides will thus be circular ribozymes, with joined ends, containing, in addition to the catalytic sequence which can be any RNA sequence capable of causing a cleavage or a modification in a target RNA sequence, an antisense type sequence complementary to the target sequence and which can consist either of RNA or of DNA or of a DNA/RNA mixture (FIG. 3).

Closed oligonucleotides coupled to molecules enabling their intracellular penetration to be increased, and especially lipophilic groups, polypeptides or proteins, also form part of the invention.

The closed oligonucleotides possess the main feature of not offering a substrate to 3' and 5' exonucleases. To acquire this property, the simplest structure is a circular oligonucleotide formed from a succession of nucleotides linked to one another via phosphodiester bonds, as indicated diagrammatically above, and possessing or otherwise intra-chain pairings (FIGS. 1A to 1C and FIG. 4).

Other structures of molecules closed with a non-3'–5' phosphodiester bond may also be synthesized and can possess a partial or total resistance to exonucleases.

Lasso-shaped molecules composed of deoxy- or ribonucleotide residues and closed either with a bond involving either the 3' end or the 5' end of the molecule (FIGS. 1A to 1C and FIG. 4B) also form part of the invention. In these lasso-shaped molecules, the linear portion can contain only a single nucleotide residue or alternatively can contain a nucleotide side chain of several residues. In these structures, one of the terminal nucleotides of the oligonucleotide is coupled to an internal nucleotide via a bond which can be formed with the base or with the sugar or with the phosphodiester group. Such oligonucleotides possess a free end and a blocked end. Resistance to exonucleases will hence be partial, it being possible for the free end to be subject to a nucleolytic degradation. The 5' and 3' ends of oligonucleotides are not sensitive in an equivalent manner to degradation, the 3' end being more sensitive. A lasso-shaped circular oligonucleotide possessing only the 5' end free is largely protected against degradation. In addition, exonucleases capable of degrading the linear portion of a lasso will be stopped at the branching point. At this stage, the oligonucleotide has become completely resistant to 3' and 5' exonucleases, irrespective of which end was initially free or branched. Such lasso-shaped molecules can contain natural or modified nucleotide residues, as stated above in the previous section. The general structure of the lasso-shaped molecules is shown in FIG. 1A and FIG. 4B.

Balloon-shaped closed oligonucleotides as described in FIG. 1A, FIG. 1B and FIG. 4C also form part of the invention. These oligonucleotides are closed with a chemical bond corresponding to an inter-chain bridging produced between two internal nucleotides. This bridging may be effected by means of a reactive—for example photoactivable—nucleotide, or alternatively by using an exogenous reagent which establishes a link between two paired regions of the oligonucleotide. Such a balloon-shaped oligonucleotide possesses only a limited number of substrate sites, or none, for exonucleases. Even if the bridging(s) closing the oligonucleotides molecule are not effected at the terminal nucleotide, only the few nucleotides localized on each side of the bridging point, at the ends of the molecule, will be accessible to the exonucleases. The exonucleases may cleave the phosphodiester bonds linking the nucleotides of the uncoupled ends, but will be stopped from the bridging site onwards. The nucleotides engaged in the bridging are totally or partially exonuclease-resistant, and thus protect the oligonucleotide against continued nucleolytic degradation.

Another family of circular oligonucleotides, closed up on themselves through a non-nucleotide molecule, also form part of the invention. These closed oligonucleotides possess a portion of their molecular structure corresponding to a DNA or RNA sequence in which the bases are unmodified and whose first nucleoside unit is linked to the last via a bond involving a molecular structure of any kind. For example, the antisense oligonucleotides may be circularized by means of a coupling between the terminal nucleotides via a protein or polypeptide structure which will be linked to the terminal nucleoside units via any type of coupling (FIG. 4). Circular oligonucleotides containing a nucleotide portion and a protein portion hence also form part of the invention. The insertion of this protein portion may be effected by various coupling methods. The protein fraction may be designed to increase the efficacy of the nucleotide molecule by different mechanisms. The protein portion may, for example, promote internalization of the oligonucleotide in cells, and enable certain cells to be targeted, where appropriate, by choosing a protein determinant used. The protein or peptide components used in the circular oligonucleotides of this type may also be signaling molecules, permitting an intracellular targeting of the oligonucleotides. For example, peptides targeted on the nucleus, originating from natural cellular or viral proteins, may be used. This aspect of the invention hence consists in proposing oligonucleotides of novel structure containing compounds capable of reacting specifically with particular receptors of the cell membrane surface, of being internalized by said cells and of exerting their biological activity inside the cell.

Circular oligonucleotides closed up on themselves via lipophilic groups or chains containing lipophilic radicals and promoting cellular internalization of these molecules also form part of the invention.

Closed oligonucleotides combined via covalent or non-covalent couplings with liposomal type encapsidation structures or any other lipoprotein or lipopolysaccharide structure also form part of the invention.

Circular oligonucleotides closed up on themselves via a phosphodiester bond, but additionally containing one or more internal bonds produced by reactive agents belonging to the structure of the molecules themselves or supplied exogenously, also form part of the invention.

These molecules will possess the characteristics of exonuclease resistance of circular oligonucleotides, and offer, in addition, particular secondary conformations capable of being adapted to the recognition of particular sites on targets themselves possessing particular secondary or tertiary conformations, whether these targets are nucleic acids or any other cellular or viral structure capable of possessing an elective and selective affinity with respect to a polynucleotide of particular primary and secondary structure.

Circular or closed antisense oligonucleotides capable of forming a triple helix with the target RNA also form part of the invention. The formation of a triple helix enables the DNA/RNA interaction between the antisense nucleotide and the target sequence to be stabilized.

Generally speaking, a circular antisense nucleotide may also be said to be a "prodrug" compound with respect to a linear antisense oligonucleotide. The cleavage of a circular oligonucleotide will give rise to a linear oligonucleotide which may exert a conventional antisense effect, with delay.

Although the compounds according to the invention will quite often contain nucleotide sequences incapable of self-pairing, closed oligonucleotides containing self-paired regions forming a double-stranded structure of variable length (see FIG. 5) also form part of the invention. This double-stranded structure may have several roles, for example that of stabilizing the molecule to permit its circularization during the synthesis of circular molecules (see the preparation methods later). This double-stranded structure may also have an active role, such as, for example, that of interacting with proteins possessing an affinity for this sequence. The double-stranded structure could correspond to a binding sequence for protein factors. In particular, an aspect of the invention is to provide stable, natural oligonucleotide molecules capable of binding cellular or viral protein factors and hence of interfering with biological processes involving these factors.

An example of the use of closed oligonucleotides containing a self-paired region—oligonucleotides intended for such an application will advantageously be simply circular—is intracellular competition with transcription factors. In this case, the double-stranded portion of the closed oligonucleotide will carry the binding sequence of the transcription factor, regulator or hormonal nuclear receptor which it is desired to trap. Interaction between the circular oligonucleotide made double-stranded and a transcription factor will lead to a reduction in the intracellular availability of this factor, and will hence modify the regulatory equilibria in which this factor participates. If it is a positive transcription factor, exercising a stimulatory effect, blockade of this factor will lead to an inhibition of the genes in question; if it is a negative factor, inhibiting gene expression after interaction with the cellular DNA, expression of these genes will then be stimulated. Generally speaking, closed oligonucleotides of the circular type, of the deoxyribo-series and containing a double-stranded portion, may interact for therapeutic purposes with any protein factor possessing an affinity for DNA and whose effects in a given pathological situation it is desired to reduce or change.

The use is also envisaged of closed, advantageously circular oligonucleotides for combining antisense and sense approaches for the purpose of greater efficacy. This method consists in simultaneously using a closed antisense oligonucleotide directed towards the messenger RNA of a transcription factor, and a closed "sense" oligonucleotide containing a double-stranded structure of sequence corresponding to the binding site of the transcription factor on the DNA. Two levels of action are hence targeted simultaneously and synergistically on the same target molecule, the antisense decreasing the synthesis of this factor and the sense molecule exerting a trapping effect on the residual molecules capable of persisting. The combined sense and antisense approaches may be used either to target the same protein at two different levels of expression and functionality, or to attack two different proteins for the purpose of seeking the greatest efficacy of the method.

This dual approach can make simultaneous use of two different molecules, one sense and the other antisense, or alternatively of a single closed oligonucleotide molecule like that described in FIG. 1C.

Another example of the use of closed oligonucleotides is intracellular competition with affinity factors for certain double-stranded RNA sequences. This is case with certain regulatory proteins which interact with messenger RNAs, especially with viral messenger RNAs. The case of the product of the HIV tat gene, which binds to a double-stranded region the the 5' end of the viral messenger RNA, may be mentioned for example. To be used as agents interacting with tat, in the case of this example, the closed—for example circular—oligonucleotides would comprise a double-stranded portion of the ribo-series, the remainder of the oligonucleotide being composed of nucleotides either of the ribo-series or of the deoxyribo-series.

Generally speaking, the closed oligonucleotides forming the subject of the invention may be used as stabilized molecules for trapping protein factors possessing an affinity for single-stranded or double-stranded nucleic acids, DNA or RNA, by mimicking both the primary structure (sequence) of the affinity sites and the possible secondary structures (hairpin structures, cruciform structures for example).

Such closed, advantageously circular, oligonucleotides, containing a nucleotide sequence recognized by protein factors, may also carry reactive groups capable of effecting bridgings, spontaneous or photo-activable, with the proteins interacting with them.

An aspect of the invention, as described in detail in the previous section, is hence to provide novel stable, natural oligonucleotides capable of being internalized in cells and of then interacting with cellular or viral factors possessing an affinity for specific nucleic acid sequences.

Circular oligonucleotides combined in pairs as a result of the complementarities of their sequences, to form a complete or partial double-stranded circular structure (capable of possessing non-pairings otherwise known as "mismatches") resistant to exonucleases, also form part of the invention. These circular double-stranded oligonucleotides may be composed of natural, rare, artificial or modified nucleotides of the deoxyribo-series or of the ribo-series. These double-stranded circular oligonucleotides could be composed of form I DNA or form V DNA, that is to say containing composite B- and Z-type structures. Form I DNA is supercoiled circular DNA whose two strands possess an interlacing. Form V DNA is a DNA whose complementary strands are not interlaced, that is to say a DNA formed from two complementary strands side by side. Double-stranded DNA can adopt different conformations, A, B or Z. The most natural and most common form of DNA is a B-type right-handed helix, whereas the less frequent Z form is a left-handed helix, more elongated than the B form. A circular structure such as that described above, containing two complementary strands not interlaced, will contain both left-handed helices and right-handed helices. Such a double-stranded circular oligonucleotides may be used as a sense type agent to interact with proteins possessing affinity for a particular sequence which will be present on the oligonucleotide in question. Such a circular double-stranded oligonucleotide, of the ribo-series in particular, may also be used generally as an immuno-stimulant, and more especially as an interferon-inducing agent. It should be noted that this potential immuno-stimulation function possessed by some RNAs may also be exploited using single-stranded circular oligonucleotides possessing self-paired double-stranded structures, as a result of the internal sequence complementarities and by turning to good account the advantage conferred by the exonuclease resistance of a circular structure.

III. PREPARATION OF CLOSED OLIGONUCLEOTIDES

The closed oligonucleotides which form the subject of the invention may be obtained chemically, biologically or by approaches making use of combinations of the techniques of synthetic chemistry and molecular biology.

The closed oligonucleotides may hence be prepared either from linear oligonucleotides, then closed up by chemical or biological techniques, or directly as oligo-nucleotides by chemical means, using reactions leading to cyclization of the molecule. These two approaches are considered successively below.

1—PREPARATION OF CIRCULAR OLIGONUCLEOTIDES FROM LINEAR OLIGONUCLEOTIDES BY LIGATION TECHNIQUES

Various methods of chemical synthesis of natural oligonucleotides have been developed, and are well known to specialists working according to the rules of the art. For example, one method consists in using a solid support known as CPG (controlled pore glass), to which the first nucleotide is bound covalently by a coupling arm through its 3'-OH end. The 5'-OH end of the nucleoside is protected by an acid-labile di-p-methoxytrityl group. This approach, employing phosphite triester chemistry and in which deoxynucleoside 3'-phosphoramidites are used as synthons, is termed the phosphoramidite method (Caruthers, 1985). This approach is the one most widely used at present and has the advantage of being completely automatic. The synthesis of an oligonucleotide from a first unit bound to CPG begins with a step of deprotection, during which the trityl group is removed, a nucleoside unit activated on its 5' group is then added, the unreactive products are blocked and a fresh cycle of deprotection/activation/coupling then begins again. Typically, the addition of a deoxynucleotide takes place according to the following four steps: i) deprotection and removal of a dimethoxytrityl protective group with acid, ii) condensation of the resulting product with a deoxynucleoside 3'-phosphoramidite, giving a deoxynucleoside phosphite triester, iii) acylation, that is to say blocking of the 5'-hydroxyl groups which have not reacted and iv) oxidation of the phosphite triester to phosphate triester. The repetition of such cycles leads to synthesis of oligonucleotides capable of extending to more than 200 units.

To quote a second example, another approach used for the synthesis of oligonucleotides is that of phosphonate chemistry (Froehler et al., 1986). This approach begins with the condensation of a deoxynucleoside 3'-H-phosphonate with a deoxynucleoside coupled to a silica glass support. Successive condensation cycles lead to the synthesis of oligonucleotide H-phosphonates. These oligonucleotides are oxidized in one step to give the phosphodiesterd.

Using one or other of these techniques, or any other sequential procedure permitting the chemical synthesis of polynucleotide chains of predetermined sequence, linear oligonucleotides which it is possible to circularize by biological means, using ligation enzymes, are obtained. To be able to use ligases to close the oligonucleotides up on themselves, the oligonucleotides must contain a 5'-P terminal group, irrespective of whether the phosphorylation of the 51 terminal has been performed chemically, or alternatively biologically using a kinase (preferably polynucleotide kinase) and ATP or any other phosphate donor.

Different procedures suitable for advantageously performing the circularization of linear oligonucleotides are described below.

1-1—A linear oligonucleotide may be circularized by establishing a partially double-stranded structure, paired to permit the functioning of a ligase, such as T4 ligase, by means of a second oligonucleotide shorter than the first and of sequence complementary to the two ends of the first oligonucleotide. In this case, illustrated in FIG. 6, the second, small oligonucleotide acts as an adaptor and makes it possible to place end to end the two terminal nucleotides of the oligonucleotide to be circularized. The action of T4 ligase, or of any other ligation enzyme capable of exerting its action on DNA, then permits circularization by forming a phosphodiester bond between these two nucleotides. This ligation can take place in solution, the two oligonucleotides being mixed in a medium permitting hybridization and ligation under suitable temperature and concentration conditions favorable to intra-chain circularization and unfavorable to inter-oligonucleotide ligations which can decrease the yield of the actual circularization reaction.

1-2—A variant of the method described in (1) consists in performing the circularization of the oligonucleotide, still by means of an adaptor, but using an oligonucleotide bound to a support which can be, for example, nitrocellulose or a derivative, a nylon membrane, a glass support, a polysaccharide structure or any other support enabling a nucleic acid fragment to be bound covalently or non-covalently and permitting subsequent hybridization between this fragment and an oligonucleotide, and which is compatible with the action of a ligase. This procedure hence consists in binding the adaptor oligonucleotide to a support, either by means of a covalent bond or via non-covalent links. It will be advantageous to use covalent bonds enabling a large number of hybridization/ligation cycles to be performed with the oligonucleotide to be circularized. The adaptor oligonucleotide may be bound to its support either at a terminal nucleotide, directly or by means of a coupling agent, or via a nucleotide located at an internal position and carrying a reactive group. A diagram showing the principle of such a method is illustrated in FIG. 6. The advantage of binding the adaptor oligonucleotide is twofold: on the one hand this binding performed under controlled physical conditions (number of molecules bound per unit area) enables the incidence of concatamer formation during the hybridization reaction following inter-oligonucleotide bonding to be reduced, and on the other hand it facilitates the production of ligation reactors, employing the adaptor oligonucleotides a large number of times for multiple circularization cycles.

1-3—The oligonucleotides may be circularized by taking advantage of secondary structures deliberately introduced by providing for sequences capable of folding back on themselves, forming partial double-stranded structures. For example, FIG. 6 illustrates the case of a "dumbbell-shaped" oligonucleotide, containing a linear portion forming a loop and containing the antisense type sequence, a double-stranded region 9 base pairs long and a closing sequence composed of $T_5$. This structure is capable of accomplishing self-pairings, thereby giving a molecule capable of being utilized as a substrate by a ligation enzyme such as T4 ligase. In this case, the yield of the ligation depends, inter alia, on the stability of the pairing at the double-stranded structure. Several pairing sequences were subjected to comparative studies, and one of the sequences permitting an advantageous circularization yield (of the order of 75%) is shown in FIG. 6. Although it does not matter which of the nucleotides might be used to produce a closing loop of variable length, from 4 to 8 residues, and mainly either A or T, will preferably be used.

The double-stranded pairing region may contain either a sequence used only for the formation of the "dumbbell" structure, or a sequence corresponding in part to the target region and which can potentially be displaced by an inter-molecular hybridization.

The experimental conditions permitting effective circularization of the oligonucleotide whose sequence is given in FIG. 6 are described in detail later in the experimental part (see "Properties and Advantages of the Closed Oligonucleotides"). In the case of this sequence, the circularization yield is of the order of 75%.

This technique was used to prepare the circular oligonucleotides which are dealt with in the experimental part.

1-4—The circular oligonucleotides may also be formed by a double-stranded structure closed up on itself at each end via a short loop of joining nucleotides. These oligonucleotides may be used for "sense" type approaches such as those described above. A typical example of a sense oligonucleotide is illustrated in FIG. 6. This oligonucleotide contains a paired sequence of 24 nucleotides and two joining loops formed by $T_5$, In the example given here, this circular oligonucleotide contains a double-stranded structure corresponding to the sequence for recognition of the hepatocyte transcription factor HNF-1. Such an oligonucleotide may be circularized simply by taking advantage of the double-stranded secondary structure formed by the complementary sequences. The closing point (that is to say the ends) of the oligonucleotide will be chosen so as to permit the greatest efficacy of circularization by intramolecular refolding. This point may be centered or more or less distal relative to the mid-point of the central secondary structure. It should also be noted that such oligonucleotides may be synthesized, not on the basis of an intramolecular reaction, but by an intermolecular reaction using two linear oligonucleotides folded back on themselves, possessing a partial double-stranded structure and generating cohesive ends capable of pairing with one another (see the diagram in FIG. 6).

1-5—A technique consisting in preparing two complementary oligonucleotides, one long and the other short, the second hybridizing in the central portion of the first, may be used to cyclize oligonucleotides which are to contain a double-stranded central region. By the action of T4 ligase, it is possible to join the two ends of the long oligonucleotide to the ends of the paired oligonucleotide, even if there are no sequence homologies permitting the formation of a self-pairing at the 3' and 5' distal sequences. Such a mechanism leads to the formation of a closed, circular oligonucleotide structure containing a central double-stranded portion.

1-6—For the preparation of circular oligonucleotides of the ribo-series (oligoribonucleotides) from linear oligoribonucleotides, the techniques which can be used are of the same kind as those described above. However it is also possible to use a enzyme, T4 RNA ligase, which is capable of spontaneously accomplishing circularization of oligonucleotides of the ribo- or deoxyribo-series. This enzyme enables linear oligonucleotides to be closed and converted to circular oligonucleotides in the presence of ATP. It is hence possible, without a special matrix and in the absence of any adaptor oligonucleotide, to circularize oligoribonucleotides in this manner. This same enzyme also enables oligodeoxyribonucleotides to be circularide, to circula much lower efficacy than in the case of oligoribonucleotides. T4 RNA ligase will advantageously be employed to circularize antisense oligonucleotides possessing a ribozyme activity, or alternatively to circularize "sense" RNAs such as, for example, the sequences interacting with HIV tat type trans-activators.

1-7—The procedures described above all involve ligation enzymes to form phosphodiester bonds and to close the linear molecules. Any enzyme enabling a phosphodiester bond to be formed between two nucleotide residues may be used to circularize oligonucleotides for the purpose of making them resistant to nuclease action, in the spirit of the invention described here, be such enzymes DNA ligases or RNA ligases. In particular, heat-stable enzymes originating from heat-resistant organisms may advantageously be used, enabling successive ligation/denaturation/hybridization cycles to be performed. To prepare the circular molecules forming the subject of the invention, either ligation enzymes in solution, or enzymes bound to a support for the purpose of enhancing the yield of the reaction and/or decreasing its cost, may be used.

Any chemical reagent permitting chemical ligation may also be used to prepare the circular molecules that form the subject of the invention. For example, and without implied limitation, reagents such as carbodiimide or cyanogen bromide could be used.

2—OTHER CHEMICAL METHODS OF PREPARATION OF THE CIRCULAR AND/OR CLOSED OLIGONUCLEOTIDES

The preparation of closed oligonucleotides for the purpose of pharmacological application, whether for animal experiments or for the preparation of pharmaceutical compounds, will advantageously employ chemical methods enabling the large quantities required to be prepared.

Several methods may be used: in particular, either linear oligonucleotides may be synthesized by the usual methods and then closed by chemical ligation or via a bond involving terminal nucleotides, or oligonucleotides capable of being subjected to a direct cyclization in the final step of the chemical synthesis may be synthesized.

2-1—Chemical Synthesis of Cyclic Oligonucleotides

Several procedures for preparing cyclic oligonucleotides have been described (Barbato et al., 1989, de Vroom et al., 1988). These approaches, in the liquid phase or on a support, enable short cyclic oligonucleotides to be obtained. For example, it is possible to use a technique which consists in binding a first nucleotide residue through the exocyclic amine group. From such a support, assembling of the oligonucleotide can take place from both 3' and 5' ends, which are protected and available. The cyclization is performed, when the synthesis is complete, using, for example, MSNT after unblocking the protective groups from the two ends.

To synthesize cyclic oligonucleotides for the purpose of manufacturing exonuclease-resistant antisense or sense molecules, any method of synthesis permitting the elongation of a polynucleotide chain from both 3' and 5' ends, and the joining of these two ends after completion of the elongation of the chosen sequence, may be used. Any method permitting the chemical joining of two independently synthesized linear oligonucleotides, subsequently recombined to form a closed structure by means of a specific chemical reaction of the ends, may be used.

2-2—Closing and Cyclization of Linear Oligonucleotides

Various methods may be used to close linear oligonucleotides in order to form closed structures forming the subject of the invention. In these structures, one or other or both of the two terminal nucleotides will be engaged in a coupling bond. Apart from the strictly circular structures described above, and which may be obtained either by ligation or by any other chemical reaction, several of the other closed structures already mentioned may be obtained by chemical coupling.

This is the case, in particular, with the lasso structures, or [sic] one of the terminal nucleotides—advantageously the 3' terminal nucleotide—is coupled to one of the nucleotides of the 5' portion of the oligonucleotide. Such structures may be obtained using modified nucleotides capable of establishing bridgings with other portions of the molecule.

It is also the case with the balloon structures, in which a bridging has been established by any agent between two or more than two nucleotides located in the terminal regions of the oligonucleotide, these regions being paired [lacuna] a small number of nucleotides, preferably over 4 to 10 nucleotides.

It is also the case with the oligonucleotides which will be closed through any group, any molecule or macromolecule permitting a coupling of the terminal nucleotides with one another, or between a terminal nucleotide and an internal nucleotide, and capable of increasing the efficacy of the compound in terms of its antisense or sense intracellular action. As an example, polypeptides for example from 5 to 100 amino acids long may be used to cyclize the oligonucleotide, it being necessary for the polypeptide linkage to have a sufficient mass to be recognized by cell receptors and to permit a better internalization or a better targeting.

IV. EXAMPLES OF USE

The closed, especially circular, oligonucleotides forming the subject of the invention described here may be used in all cases where it will be advantageous to have at one's disposal an oligonucleotide possessing an increased resistance to exonucleases compared with a linear oligonucleotide.

The closed oligonucleotides may, in particular, be used as antisense or sense agents to act specifically on the transcription or translation of protein(s) whose level of expression it is desired to modulate for the purpose of research or therapy.

The few possible applications which are given below are merely non-exhaustive examples, in no way limiting, of situations in which it might be possible to envisage an antisense, or sense, type approach, and where the use of natural exonuclease-resistant oligonucleotides possessing the lowest possible toxicity would offer an advantage.

More especially, the compounds according to the invention are usable as a therapeutic agent, in particular as an antiviral or anticancer agent, especially in pharmaceutical compositions for external topical application or for systemic use.

However, they can also be inducers of natural immunomodulators such as interferon. It is also possible to use them in diagnosis in vitro or in vivo.

Generally speaking, the closed oligonucleotides, natural and circular in particular, will find especially suitable spheres of application in the field of dermatology, on account of the accessibility of the targets to be treated and the minimal or nonexistent toxicity of these compounds. All dermatological conditions which may be dependent on a mechanism of genetic dysfunction and for which an etiological factor may be identified and whose gene and/or messenger RNA sequence may be known will enable an antisense approach—or even a "sense" approach in some favorable cases—to be potentially envisaged.

The use of natural oligonucleotides, which hence possess the lowest toxicity, enables the possibility of this kind of approach to be envisaged for serious or minor conditions, and even, where appropriate, for uses of the cosmetological type, that is to say on healthy skin and in a field of application where the toxicities of the products must be as low as possible.

Besides the viral targets defined later, many dermatological diseases could be treated with exonuclease-resistant circular or closed natural oligonucleotides. Among the potential targets of such approaches, inflammatory diseases such as atopical dermatitis or lupus erythematosus, keratinization diseases such as ichthyosis and psoriasis and neoplastic diseases such as melanoma or cutaneous T lymphoma. Thus, for example, circular antisense oligonucleotides applied in dermatology could be directed towards messenger RNAs of inflammation mediators such as interleukins, towards messenger RNAs of proteins involved in disorders of proliferation of the epidermal cells or alternatively towards messenger RNAs coding for proteins possibly involved in phenotypic skin aging, such as, for example, collagenase, elastase and transglutaminases.

More generally speaking, the closed oligonucleotides, natural and circular in the main, could, for example, be used as antisense, or sense, antiviral agents, either for topical (dermatological) indications or for systemic indications. For example, such oligonucleotides could be used as antiherpetic (HSV-1 and HSV-2, CMV, EBV) agents, as antipapillomavirus (cutaneous, genital, laryngeal or other HPV) agents, as antihepatitis (HBV, HCV, HDV) agents, as anti-HIV (HIV-1 and HIV-2) agents, as anti-HTLV (HTLV-1 or HTLV-2) agents, and the like.

These circular oligonucleotides could also be used as agents for repressing the expression of certain cellular proteins directly responsible for or involved in the etiology of diseases of cell proliferation and differentiation. For example, these circular oligonucleotides could be directed towards the expression of cellular oncogenes which are hyperexpressed or expressed in an uncontrolled manner in tumor cell types (RAS, ERB, NEU, SIS, MYC, MYB, and the like).

In particular, these natural circular oligonucleotides resistant to serum exonucleases could be used as antisense agents directed towards messenger RNAs of oncogenes expressed in leukemic cells and involved in their proliferation, or alternatively as "sense" agents directed towards proteins having affinity for certain DNA sequences and expressed at pathological levels in some of these proliferative diseases. In the context of the treatment of certain leukemias, for marrow transplants, the circular, closed oligonucleotides may be used in the context of "ex vivo" applications.

For these many indications, it will be possible to establish appropriate pharmaceutical dosage formulations in order to optimize the delivery of these molecules to their target cells. Thus, for example, closed, especially circular, oligonucleotides may be encapsulated in liposomes, nanoparticles or LDL particles, or in any other type of microsphere permitting appropriate preservation and promoting targeting. The closed, for example circular, oligonucleotide molecules could also be combined with cationic surfactants. It is quite obvious that these few examples are neither exhaustive nor limiting.

The closed, especially circular, oligonucleotides forming the subject of the invention described here are hence capable of being included in all kinds of pharmaceutical preparations, at concentrations which vary according to the indication.

In particular, the dermatological applications mentioned above will require the preparation of creams, solutions, emulsions, lotions, gels, sprays, powders, aerosols, and the like, prepared by combining the circular—or closed—oligonucleotide of chosen sequence with the common pharmaceutical components participating in the composition of these products. For example, for preparations intended for topical applications in dermatology, the circular, or closed, oligonucleotides may be combined with all kinds of preservatives such as methyl or propyl hydroxybenzoate or benzalkonium chloride, for example, and other stabilizing, emulsifying, dispersing, suspending, solubilizing, coloring and thickening agent, fragrances, and the like. It should be noted that some of these compositions, especially the compositions intended for topical applications for dermatological indications, may combine both circular—or closed— oligonucleotides with other active principles such as, for example, bacteriostatic or antiseptic or antimicrobial or antibiotic or analgesic or antipruritic agents, and the like.

All these examples are given only to illustrate the intention and are neither exhaustive nor limiting.

V. PROPERTIES AND ADVANTAGES OF THE CLOSED OLIGONUCLEOTIDES

The experimental examples are given below to illustrate the advantages of a closed oligonucleotide over a linear "open" oligonucleotide of the same sequence. These examples are taken from experiments carried out with oligonucleotides circularized according to the method described in the part "production of closed oligonucleotides", section 1–3. The closed oligonucleotides dealt with here are hence circular oligonucleotides composed of natural nucleotides linked to one another via unmodified phosphodiester bonds.

BRIEF DESCRIPTION OF THE DRAWINGS

Reference is made in the description and the examples to the attached figures, to which the following legends apply.

Figure 6A:
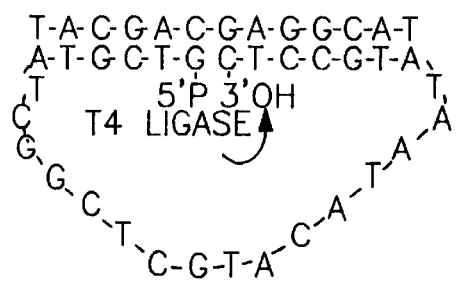
FIG. 6:
A—Circularization of a linear oligonucleotide using a partially complementary oligonucleotide as a guide and T4 ligase SEQ ID NO. 8 (short strand) and SEQ ID NO. 9 long strand.
B—Circularization of a linear oligonucleotide using a partially complementary oligonucleotide as a guide bound to a support and T4 ligase SEQ ID NO. 8 (short strand) and SEQ ID NO. 9 long strand.
C—Circularization of an oligonucleotide containing a self-pairing region by means of T4 ligase SEQ ID NO. 10.
D—Example of bimolecular reaction between two self-paired oligonucleotides possessing cohesive ends, enabling a oligonucleotide carrying a long double-stranded region and two adaptation loops to be generated SEQ ID NO. 11 (right hand sequence) adn SEQ ID NO. 12 (left hand sequence) and SEQ ID NO. 2 (circular sequence).
Figure 6B:
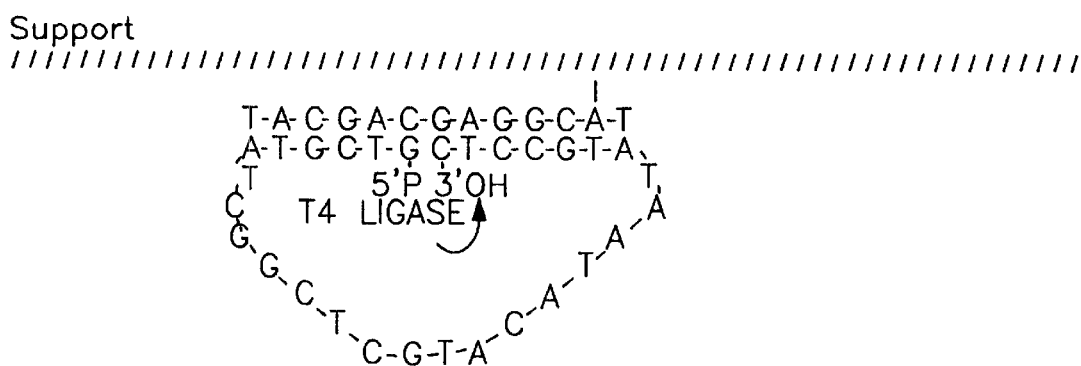
Figure 6C:
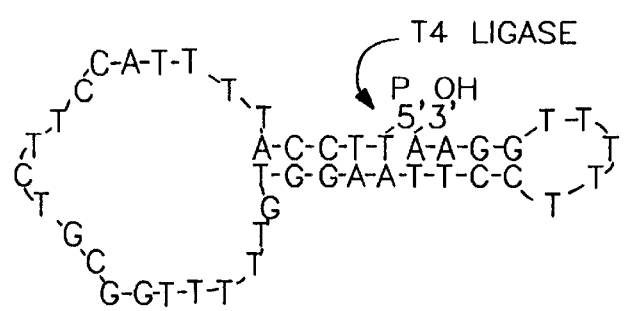
Figure 6D:
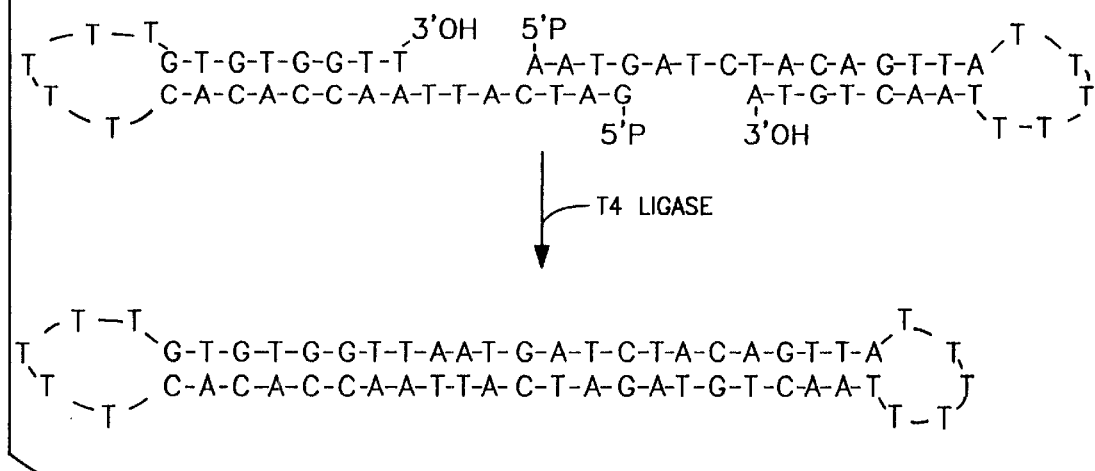

The sequence of the oligonucleotide c7 is that described in FIG. 6C; the oligonucleotides c6 and c8 are composed of different sequences but ones which can adopt the same type of structure as c7, that is to say a closed structure with a central double-stranded portion.

The conditions of ligation of the oligonucleotides c6, c7 and c8 are those described in "Properties and Advantages of the Closed Oligonucleotides—1". 1 µg of radioactive oligonucleotide originating from the ligation reaction (lanes 5 to 8) or 1 µg of corresponding linear oligonucleotide (lanes 1 to 4) were analyzed on 15% polyacrylamide gel/7M urea without subsequent treatment (lanes 4 and 5) or after incubation with alkaline phosphatase (lanes 3 and 6), with exonuclease VII (lanes 2 and 7) or with phosphodiesterase I (lanes 1 and 8) under the conditions described in "Properties and Advantages of the Closed Oligonucleotides—2".

L indicates the position of migration of the linear oligonucleotides; C indicates the position of migration of the closed oligonucleotides.

B—Autoradiograph of a polyacrylamide gel on which linear or circular oligonucleotides have been caused to migrate after incubation in the presence of serum.

1 µg of radioactive oligonucleotide c7 (whose sequence is given in FIG. 6C), linear (L) or closed (C), was prepared and purified as described in "Properties and Advantages of the Closed Oligonucleotides—1". After incubation at 37° C. for the times indicated in the presence of DMEM containing 10% fetal calf serum, the products were analyzed on 15% polyacrylamide gel/7M urea under the conditions detailed in "Properties and Advantages of the Closed Oligonucleotides—3".

C—Graphic representation of the degradation (measured by analysis on gel as described above) of the oligonucleotides c7L (linear) and c7C (circular) after incubation in 10% fetal calf serum, as described above, from time t=0 to time t=96 hours. To obtain a quantification, the gel fragments corresponding to the localization of the bands observed by autoradiography were cut out, and their radioactivity was measured by counting in a scintillation counter. The results are expressed as a percentage degradation relative to the radioactivity at time t=0.

FIG. 8:

A—Autoradiograph of a non-denaturing polyacrylamide gel on which linear or circular oligonucleotides have been caused to migrate after hybridization with oligonucleotides containing complementary sequences of the deoxyribo- or ribo-series.

300 ng of the closed radioactive oligonucleotide c7 (C) or 160 ng of the linear oligonucleotide c7 (L) were incubated with increasing quantities of a non-complementary oligonucleotide (lanes a to g) or of a 42-mer oligonucleotide (12; lanes h to n) complementary to 21 nucleotides of the large loop of c7 (FIG. 6C). The quantity of cold oligonucleotide added is 0 (lanes a and h), 30 ng (b and i), 60 ng (c and j), 150 ng (d and k), 300 ng (e and l), 750 ng (f and m) or 1500 ng (g and n). After hybridization under the conditions described in "Properties and Advantages of the Closed Oligonucleotides—4-1", the products were analyzed on 20% non-denaturing polyacrylamide gel.

The arrows indicate the positions of the closed (C) and linear (L) oligonucleotides c7 and of the c7L/12 and c7C/12 hybrids.

B—Autoradiograph of a denaturing polyacrylamide gel on which linear or circular oligonucleotides, hybridized or otherwise with oligonucleotides containing a complementary region and then treated with S1 nuclease, have been caused to migrate.

Figure 8A:
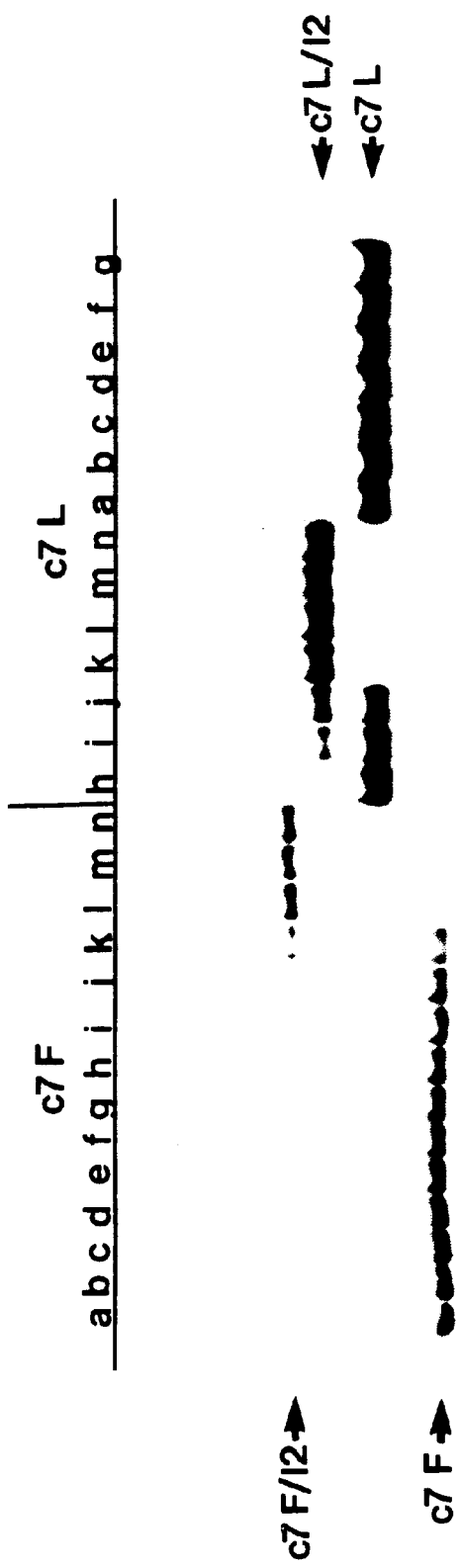

300 ng of closed (C) or linear (L) oligonucleotide c7, synthesized urified as described in FIG. 8A, or 300 ng of a cold 42-mer oligonucleotide (12), were incubated with 1 ng of an RNA 43 nucleotides long transcribed in vitro and labelled with $^{32}$P to high specific activity ("Properties and Advantages of the Closed Oligonucleotides—4-2"). The 43-mer RNA contains 27 bases complementary to the 21 nucleotides of the large loop plus 6 nucleotides of the self-paired region of c7C (FIG. 6C); it is also complementary to 37 bases of the 42-mer oligonucleotide 12. After hybridization, the products are analyzed on 20% polyacrylamide gel/7M urea directly (lane 1) or after incubation for 3 minutes (lane 3) or 30 minutes (lane 4) in the presence of Si nuclease or 30 minutes in the absence of S1 nuclease (lane 2) under the conditions described in "Properties and Advantages of the Closed Oligonucleotides—4-2". The left part of the figure (--) shows the results obtained with the 43-mer RNA incubated alone. Lane 5: 43-mer RNA which has not undergone any treatment subsequent to transcription.

The arrows indicate the positions of the 43-mer RNA, closed c7 (C) and linear c7 (L) oligonucleotides, as well as those of the protected RNAs (RNA 37, 27 and 21).

C—Autoradiograph of a denaturing polyacrylamide gel on which linear or circular oligonucleotides, hybridized or otherwise with oligoribonucleotides containing a complementary region and which were then treated with RNase H, have been caused to migrate.

Figure 8B:
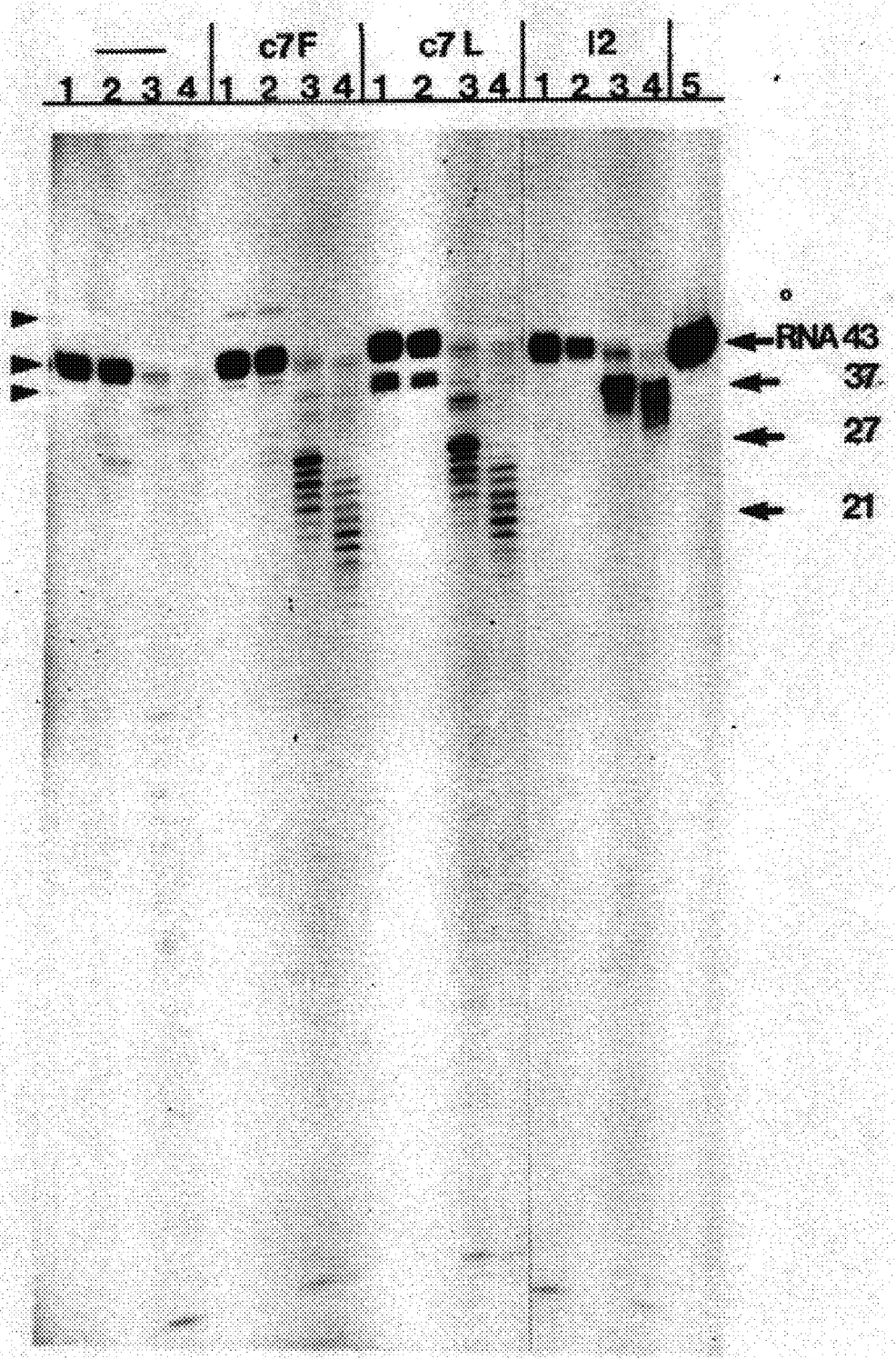

The oligonucleotides tested (RNA 43, c7C, c7L and 12), as well as the hybridization conditions, are the same as those described in FIG. 8B. After ybridization, the products of the reaction were incubated in the absence (−) or presence (+) of RNase H and analyzed on 20% polyacrylamide gel/7M urea under the conditions described in "Properties and Advantages of the Closed Oligonucleotides—5". The arrows indicate the positions of the 43-mer RNA, closed c7 (C) or linear c7 (L).

FIG. 9:

Analysis of the effects of linear or circular oligonucleotides on cell growth.

FIG. 10:

Study of the inhibitory effects of linear or circular antisense oligonucleotides on the multiplication of the HSV-1 virus.

FIG. 11:

Retarding gel illustrating the binding of the transcription factor HNF-1 by double-stranded linear or circularization [sic] closed, sense type oligonucleotides. The abbreviations used in this legend relate to the nomenclature used in Example 7.

| 01 | HNF-1 DSL without nuclear extract |
|---|---|
| 02 | HNF-1 DSL +1 µg liver nuclear extract |
| 03 | HNF-1 Cr1 without nuclear extract |
| 04 | HNF-1 Cr1 +1 µg liver nuclear extract |
| 05 | HNF-1 Cr1 unligated without nuclear extract |
| 06 | HNF-1 Cr1 unligated +1 µg liver nuclear extract |
| 07 | HNF-1 Cr2 without nuclear extract |
| 08 | HNF-1 Cr2 +1 µg liver nuclear extract |
| 09 | HNF-1 Cr2 unligated without nuclear extract |
| 10 | HNF-1 Cr2 unligated +1 µg liver nuclear extract |
| 11 | HNF-1 Cr3 without nuclear extract |
| 12 | HNF-1 Cr3 +1 µg liver nuclear extract |
| 13 | HNF-1 Cr3 unligated without nuclear extract |
| 14 | HNF-1 Cr3 unligated +1 µg liver nuclear extract |

HNF-1Cr1, Cr2, Cr3 represent 3 different preparations of the sense oligonucleotide HNF-1 Cr.

EXAMPLE 1

Figure 7C:
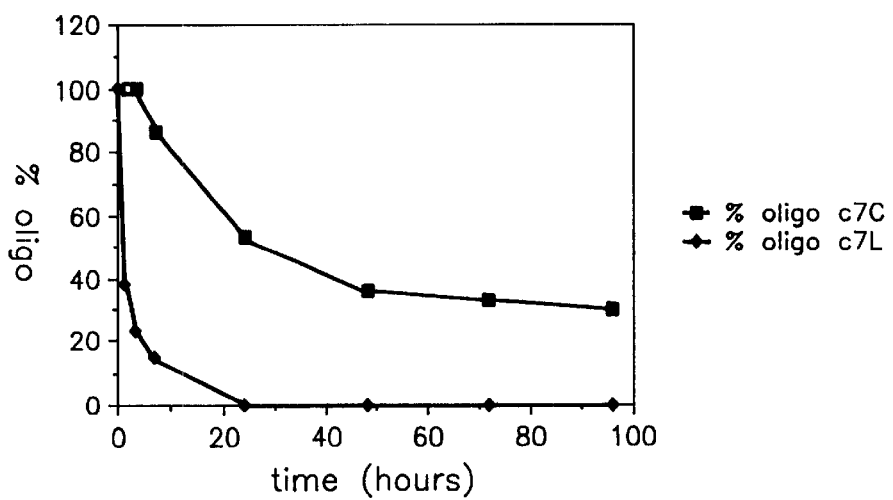
FIG. 7:
A—Autoradiograph of a polyacrylamide gel on which various oligonucleotides (circular and linear) have been caused to migrate after treatment with different exonucleolytic enzymes.
Figure 7A:
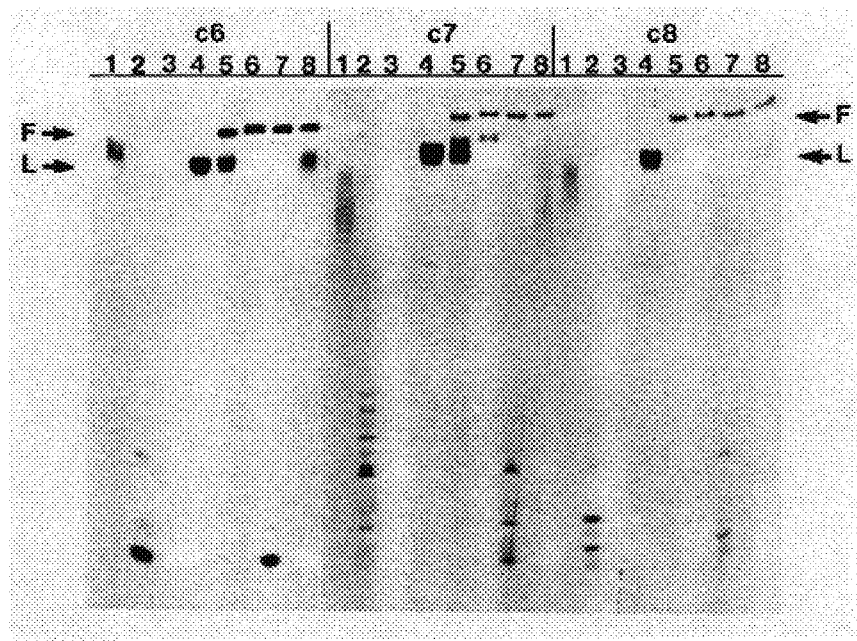

Production of Closed Oligonucleotides Containing a Self-pairing Region by Means of T4 DNA Ligase The experimental conditions permitting effective closure/ligation of the oligonucleotides whose sequences are given in FIG. 7A are as follows: 11 µM linear oligonucleotide labelled at the 5' end with g $^{32}$P [sic] ATP (150 µg; specific activity=2–3×10$^5$ cpm/µg), 50 mM Tris-HCl pH 7.8, 10 mM MgCl$_2$, 20 mM DTT, 1 mM BSA on M ATP and 10,000 units of T4 DNA ligase (2,000 u/µl; New England Biolabs) in a total volume of 1 ml. After incubation for 48 hours at 4° C., the reaction mixtures are extracted with phenol/chloroform/isoamyl alcohol, precipitated with absolute ethanol, washed with 80% ethanol and dried. The ligation products are then separated from the unligated oligonucleotide by denaturing electrophoresis on 20% polyacrylamide gel/7M urea. The positions of the oligonucleotides may be observed directly by fluorescence interference, irradiating at 212 nm the gel placed on a plate containing a chromophore which fluoresces in ultraviolet light, or alternatively by autoradiography. The ligated monomeric oligonucleotide is characterized by a migration which is slowed down relative to its unligated homolog (FIGS. 7A and B). The bands corresponding to the closed monomeric oligonucleotide and to its unligated linear homolog are excised from the gel, and DNA is isolated by conventional techniques of extraction from polyacrylamide gels. In the case of the sequences in question, the yield of formation of the closed monomeric oligonucleotide is of the order of 65 to 75%.

Alternatively, the products of the ligation reaction may be analyzed without prior purification, directly after inactivation of the DNA ligase by heating the ligation medium for 2 minutes at 90° C.

EXAMPLE 2

Resistance of the Circular Oligonucleotides of the Deoxyribo-series to Nucleases and to Phosphatases We compared the resistance of the circular and linear oligonucleotides to the action of alkaline phosphatase (phosphomonoesterase hydrolyzing the 3' and 5' phosphates of DNA and of RNA), exonuclease VII (exodeoxyribonuclease digesting single-stranded DNA from both 3' and 5' ends) and phosphodiesterase I (exonuclease digesting DNA or RNA from the 3'-OH).

For this experiment, the [5 '-$^{32}$P]oligonucleotides whose sequences are shown in FIG. 7A were prepared as described above (section 1). After ligation, the reaction mixtures were heated for 2 minutes at 90° C. in order to inactivate the DNA ligase.

1 μg of oligonucleotide originating from the ligation reaction, or 1 μg of the uncircularized homologous linear oligonucleotide used as a control, was incubated at 37° C. in a volume of 10 μl of 50 mM Tris HCl pH 7.5, 10 MM MgCl$_2$, 20 mM DTT in the presence of 1 unit of calf intestinal phosphatase (CIP) or 1 unit of *E.coli* exonuclease VII for 1 hour, or 5×10$^{-5}$ units of *Crotalus durissus* phosphodiesterase I for 10 minutes. After incubation, the products of the reaction are analyzed on 15% polyacrylamide gel under denaturing conditions. The result of the gel is shown in FIG. 7A.

It is observed on the autoradiograph of this gel that:
 the circular, closed oligonucleotides are resistant to phosphatase whereas the linear oligonucleotides are sensitive thereto;
 the circular, closed oligonucleotides are resistant to the action of exonuclease VII whereas the linear oligonucleotides are sensitive thereto;
 the circular, closed oligonucleotides are resistant to the action of phosphodiesterase I whereas the linear oligonucleotides are sensitive thereto.

This experiment shows that the oligonucleotides prepared as described above are indeed covalently closed circular molecules, and that these molecules possess a total resistance to exonucleolytic enzymes.

EXAMPLE 3

Resistance of the Closed, Circular Oligonucleotides to Serum Nucleases

Figure 7B:
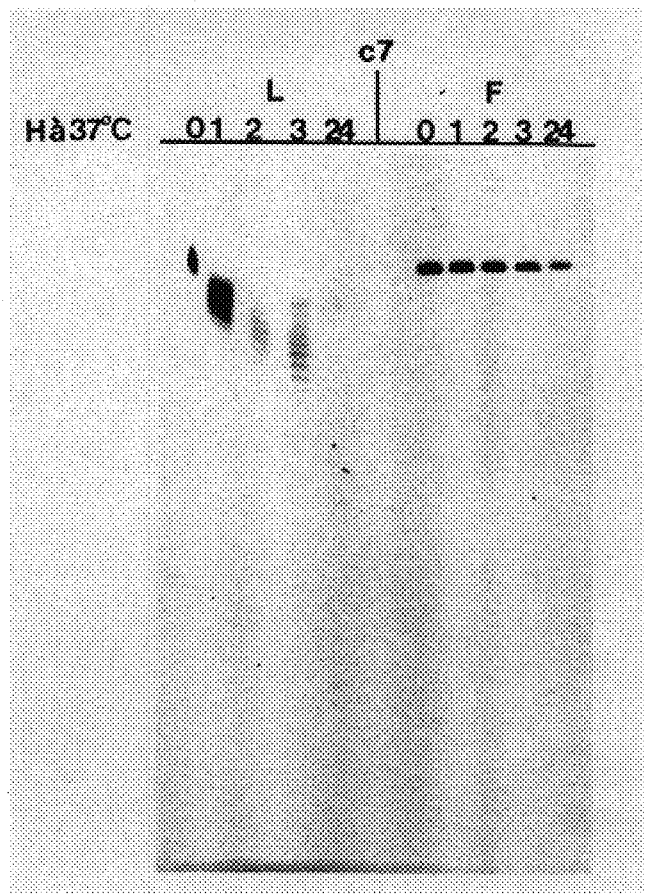

The circular, closed oligonucleotides possess a resistance to nucleolytic degradation which is greater than that of the linear oligonucleotides when they are incubated in the presence of serum. 1 μg of closed oligonucleotide and 1 μg of corresponding linear oligonucleotide, prepared and purified after ligation as described in section 1, are incubated at 37° C. in 10 μl of DMEM medium containing 10% fetal calf serum. The speed of the reaction is monitored up to 96 hours, and the samples taken at intervals of time are analyzed on 15% polyacrylamide gel under denaturing conditions. The autoradiograph of a gel analyzing the degradation over 24 hours is shown in FIG. 7B.

FIG. 7C is the graphic representation of a study over 96 hours of the degradation of a linear oligonucleotide (c7L) in comparison with the degradation of a circular oligonucleotide (c7C) under the conditions described above. This graph demonstrates the considerable differences in stability between these two types of oligonucleotides.

These experiments enable the following conclusions to be drawn:
 the linear oligonucleotides are rapidly degraded by the nucleases in the serum. The degradation takes place from the first minutes of the incubation, and is complete after a few hours;
 the half-life of an unmodified normal linear oligonucleotide is much less than 1 hour, it being possible for this time to vary slightly in a positive or negative direction according to the serum used;
 the degradation of the linear oligonucleotides is progressive, and the appearance of degradation products of decreasing length, becoming progressively shorter with the passage of time, is observed, indicating that the degradation is mainly the result of exonucleases, and especially of 3' exonucleases;
 in contrast, the closed oligonucleotides are resistant to nucleolysis by serum enzymes, and less than 60% conversion to degradation products is observed even after 96 hours (4 days) of incubation at 37° C.
 the half-life of a closed, circular oligonucleotide in serum is much longer than 24 hours.

These results confirm that the degradation of the antisense oligonucleotides in serum is mainly the result of exonucleases and not of endonucleases, and demonstrate the resistance of the closed oligonucleotides to degradation.

Natural closed oligonucleotides not carrying particular chemical modifications possess a resistance to serum nucleases similar to the resistance described for modified derivatives. This experiment hence shows that, under standard conditions of incubation of oligonucleotides in the presence of serum, the closed oligonucleotides which form the subject of this patent possess a significant advantage over linear oligonucleotides.

EXAMPLE 4

Hybridization of Closed Oligonucleotides of the Deoxyribo-series With DNA and RNA To possess an antisense effect, antisense oligonucleotides must be able to hybridize with their target under satisfactory conditions of stability. We analyzed the hybridization between closed oligonucleotides and polynucleotides carrying complementary sequences, either of the ribo-series or of the deoxyribo-series.

EXAMPLE 4-1

Demonstration of the Hybridization Between a Closed Oligonucleotide and a Liner DNA 300 ng of closed, circular oligonucleotide, prepared and purified as described above—or 160 ng of the linear homologous oligonucleotide as a control—are incubated with a cold oligomer 42 nucleotides long containing a sequence of 21 nucleotides complementary with the 21 bases forming the large loop in the closed structure (see the sequence of FIG. 6C). The mole ratios of the labelled oligonucleotide to the cold complementary oligonucleotide vary from 10:1 to 1:5. Hybridization takes place for 1 hour at 37° C. in 1×SSC (150 mM NaCl, 15 mM Na$_3$ citrate, pH 7.0). After incubation, the products are analyzed on non-denaturing 20% polyacrylamide gel. The results of autoradiography of the gel are shown in FIG. 8A.

It is observed on this gel that the speeds of shifting of the bands between the single-stranded and double-stranded positions are identical for the linear oligonucleotides and the closed oligonucleotides. This result means that the efficacies of hybridization between a closed oligonucleotide and a complementary DNA are identical to those of a linear oligonucleotide with a complementary sequence.

EXAMPLE 4-2

Malping of the Hybridization Between a Closed Oligonucleotide and a Linear RNA

The following experiment consists in analyzing, by the S1 nuclease protection technique, the position of the double-stranded regions on hybridization between a closed deoxyribonucleotide and an oligoribonucleotide containing a sequence which is complementary to the looped region of the closed oligonucleotide. S1 nuclease is an endonuclease specific for single-stranded nucleic acids, digesting only unpaired sequences. It is an enzyme which enables the regions which are in double-stranded form to be mapped and to be differentiated from the single-stranded regions.

A closed oligonucleotide, synthesized and purified as described above, is incubated with a linear RNA 43 nucleotides long containing a sequence of 27 bases complementary to the 21 nucleotides of the loop of the closed oligonucleotide and to 6 of the nucleotides engaged in the self-paired region (see the sequence of FIG. 6C). This RNA was transcribed with T7 RNA polymerase from a synthetic template, and labelled with [α-$^{32}$P]-ATP to a high specific activity (2.3×10$^8$ cpm/μg). After transcription, the transcribed RNA is purified by electrophoresis on 15% polyacrylamide gel/7M urea, eluted from the gel and precipitated with ethanol, then suspended in water.

After incubation of 300 ng of closed oligonucleotide or of its linear homolog for 1 hour at 37° C. with 1 ng of RNA in 0.15 M NaCl, 0.1 M Hepes pH 7.9, 0.3 mM EDTA, the reaction mixture is diluted 10 times in 50 mM NaCl, 33 mM sodium acetate pH 4.4 and 30 μM ZnSO4, and 4 units of S1 nuclease are added. Aliquot samples are taken after 3 minutes and 30 minutes of digestion at 37° C., and the products obtained are analyzed on 20% polyacrylamide gel under denaturing conditions. As a control, the radioactive RNA has also been incubated under identical conditions in the presence of a linear oligonucleotide complementary to the RNA over 37 nucleotides.

The results of this experiment are shown in FIG. 8B.

It is observed on this gel that:
the RNA incubated in the absence of complementary oligonucleotide or in the presence of a non-complementary oligonucleotide is, in fact, not hybridized and is completely digested by S1 nuclease;
the RNA incubated with a control linear oligonucleotide is protected from digestion over a length of 37 nucleotides, which corresponds to the length of the complementary sequences; after 30 minutes of incubation, the protection profile is shifted towards the bands centered around two predominant bands of 35 and 4 nucleotides, respectively, which may correspond to a "breathing" of the double-stranded molecule;
the RNA incubated with the closed oligonucleotide possesses a characteristic protection profile, with several bands spread according to a distribution centered around a band 27 nucleotides in length corresponding to the predominant band; after 30 minutes of incubation, the predominant protected bands are located at 20 and 21 nucleotides;
the protection profile observed on incubation of the RNA with an oligonucleotide of the same sequence as the circularized oligonucleotide, but linear, is identical to that of the circularized oligonucleotide;
the pattern of protection of RNA by the closed oligonucleotide hence shows that hybridization between the RNA and the circular loop of the oligonucleotide takes place over an optimal length of 21 nucleotides, thus comprising the whole of the loop. The complementary RNA can even displace the paired nucleotides in the double-stranded portion of the oligonucleotide to hybridize therewith.

This experiment demonstrates that hybridization between a closed oligonucleotide and an RNA containing a region complementary to the loop can take place under standard conditions of temperature and ionic strength, and that the hybrid thereby formed possesses the normal characteristics of a double-stranded molecule resistant to S1 nuclease.

EXAMPLE 5

Activation of RNase H Activity by a Hybrid Formed Between a Closed, Circularized Oligonucleotide and a Linear RNA It is known that the antisense effects of oligonucleotides complementary to a messenger RNA are, in many cases, the result of an action of cellular RNase H on the substrate thereby formed. RNase H is an enzymatic activity which degrades RNA when it occurs in the form of an RNA/DNA hybrid. We hence checked that hybridization between a closed antisense oligonucleotide and a linear RNA did indeed create a substrate for RNase H.

The structure of the linear RNA used for this experiment and also its preparation were described in the section above.

Figure 8C:
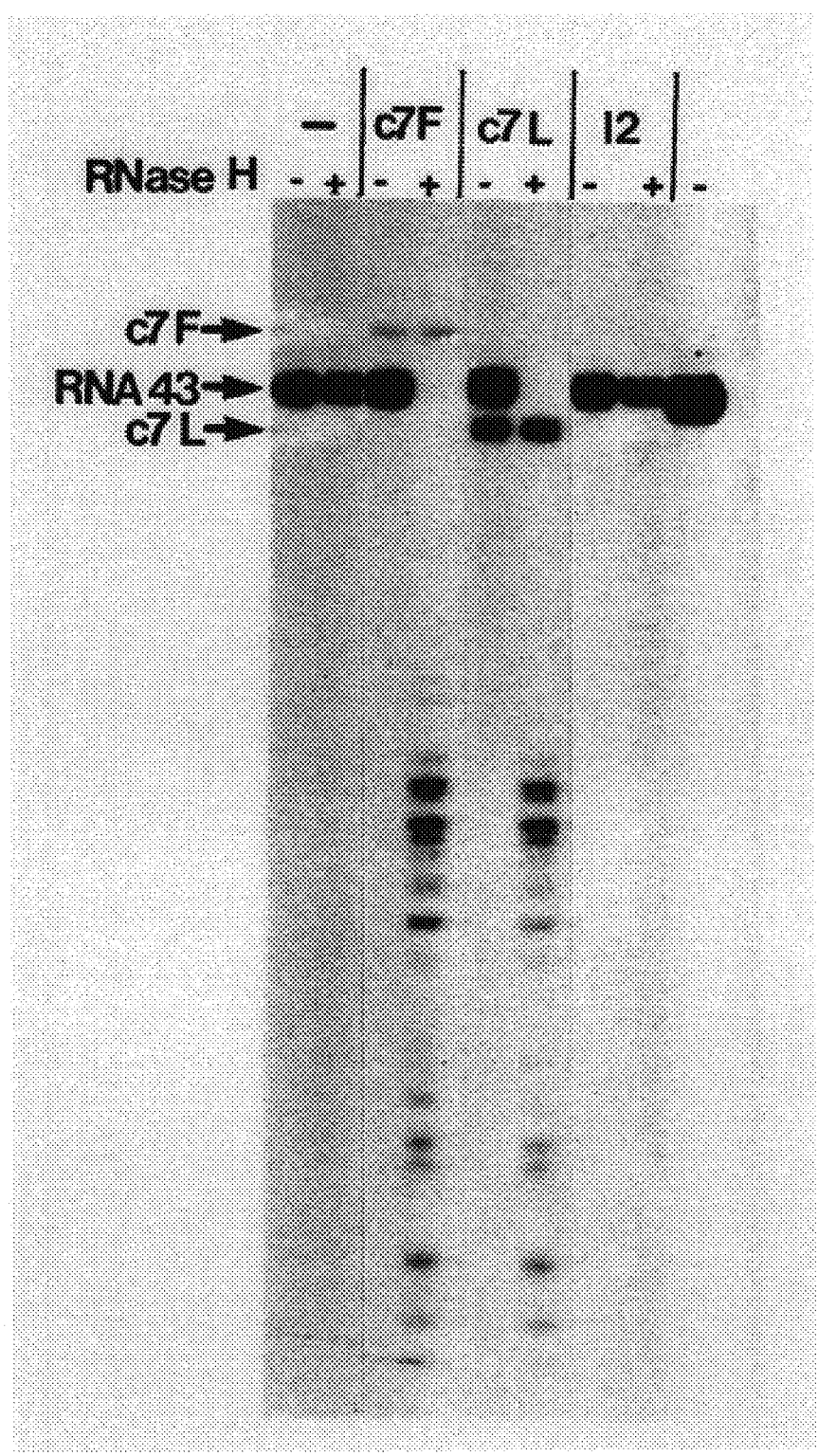

The hybridization of 300 ng of closed oligonucleotide or of its linear homolog with 1 ng of radioactive RNA (2.3×10$^8$ cpm/μg) containing a region complementary to the looped portion of the antisense oligonucleotide is carried out under the conditions described in section 4-2. These conditions provide for a hybridization of the whole of the RNA with the complementary DNA. The hybridization reaction will be said to be "driven" by the DNA. After incubation, the volume is diluted 10-fold, adjusting the incubation buffer to 20 mM Tris HCl pH 7.5, 100 mM KCl, 10 mM MgCl$_2$, 0.1 mM DTT, and 2 units of RNase H are added. The mixture is incubated at 37° C. for 20 minutes, and the products of the reaction are analyzed as above. The results of the gel are shown in FIG. 8C.

It is observed on this gel that:
the labelled RNA not hybridized with a complementary DNA sequence is completely resistant to the action of RNase H;
the labelled RNA 43 nucleotides long hybridized with a control linear oligonucleotide complementary to 37 bases of the RNA becomes partially sensitive to the action of RNase H, and gives degradation products;

the labelled RNA hybridized with a closed oligonucleotide whose loop is complementary to 21 nucleotides of this RNA becomes very sensitive to the action of RNase H, and gives a series of degradation products whose lengths are compatible with the analyses of S1 protections described in the section above.

In fact, the experiment of induction of substrate for RNase H is the mirror image of the experiment of S1 protection, and the results obtained in both cases are entirely consistent, both indicating similar hybridization positions and showing that a substrate for RNase H may be created by hybridization between a linear RNA and a circular oligodeoxyribonucleotide.

This experiment hence shows that a linear RNA partially hybridized with a closed oligodeoxyribonucleotide becomes a substrate for RNase H, implying that a circular DNA hybridized with a target messenger RNA can exert an antisense effect through the action of this enzyme on a substrate generated in this manner. In addition, this experiment also shows that, under identical experimental conditions of concentration, the circular RNA/DNA substrate gives rise to a greater degradation by RNase H than the linear RNA/DNA substrate. Under identical conditions, all other factors being equal, circular antisense oligodeoxyribonucleotides hence possess a further advantage over linear antisense oligonucleotides.

EXAMPLE 6

Inhibition of the Multiplication of Herpes Simplex Type 1 Virus (HSV-1) by Circular Antisense Oligonucleotides The oligonucleotide GT, whose sequence is given below, was synthesized, circularized or otherwise, and used in the experiments described here, either in linear form or in circular form.

1-Experimental Protocols

Sequence and Circularization of the Oligonucleotide GT

Sequence of GT: 5' GTG GGA CGT TCC TCC TGC GGG AAG CGG C 3' (SEQ ID NO. 13)

To permit an effective chemical circularization, the oligonucleotide GT was synthesized in the 3'P form, and circularized by positioning the 5' and 3'P ends by hybridization with the oligonucleotide of the following partially complementary sequence: 5° C.CA CGC CG 3'

The ligation conditions used are as follows: for 100 µg of oligonucleotide GT: 100 µg of complementary oligonucleotide 5 0.25 M MES, pH 7.4
mM $MgCl_2$
0.2 M CnBr [sic]
Reaction volume: 500 µl
Incubation at 4° C. for 30 minutes. The reaction is stopped by adding 1/10 volume of 3M sodium acetate and 2.5 volumes of absolute ethanol, the oligonucleotides precipitated and purified on denaturing polyacrylamide gel.

Infection of Cells in the Presence or Absence of Antisense Oligonucleotides

The cells (Vero ATCC cells—passage 121—cultured in MEM medium (Gibco) supplemented with 5 or 10% of FCS, L-glutamine, non-essential amino acids and penicillin/streptomycin) are subcultured on the day before infection at a density of $5 \times 10^4$ cells per 2-$cm^2$ well. 16 to 24 hours later, the cells are infected with HSV1F at a multiplicity of infection of 3 pfu/cell in the presence or absence of oligonucleotides.

The oligonucleotides are diluted in culture medium without serum at 2× concentration relative to the desired final concentration, and added in a volume of 50 µl. The virus is also added in a volume of 50 µl, 5 min after the oligonucleotides. The cells are hence treated with a volume of 100 µl (50 µl oligonucleotides +50 µl virus) for one hour at 37° C. with gentle agitation every 15 min. Alternatively, the oligonucleotides may be added several hours before infection.

After one hour of incubation, the medium is aspirated off and 500 µl of complete medium are added to the cells. Incubation is continued for 24 h before being stopped by freezing plates in liquid nitrogen.

All the inhibition measurements are performed in duplicate or triplicate.

Titration of the Virus

The viruses are recovered directly in the culture edium after 3 cycles of rapid freezing in liquid nitrogen/thawing at 37° C. They are then diluted in medium without serum to perform the actual titration.

The indicator cells are subcultured on the previous day in complete medium on the basis of $10^5$ cells/2 $cm^2$ well.

The next day, the medium is aspirated off and 100 µl of the different dilutions are introduced into each well. After incubation for one hour at 37° C. with agitation every 15 min, the medium is aspirated off and the cells are covered with complete medium containing 1.2% of methyl cellulose (2.5% final serum concentration) for 3 days at 37° C.

After 3 days, the medium is removed and the cells are fixed with PBS/10% formalin (37% solution) for 20 min and then stained with 2% crystal violet (in PBS/20% ethanol) for 20 min. The plates are then rinsed and the plaques are counted by transparency on a negatoscope.

The titration [sic] are performed in duplicate for each point.

The calculations of inhibition are performed relative to the viral titers observed in the absence of oligonucleotide.

2—Results

Analysis of the effects of circular oligonucleotides on cell growth

Figure 9:
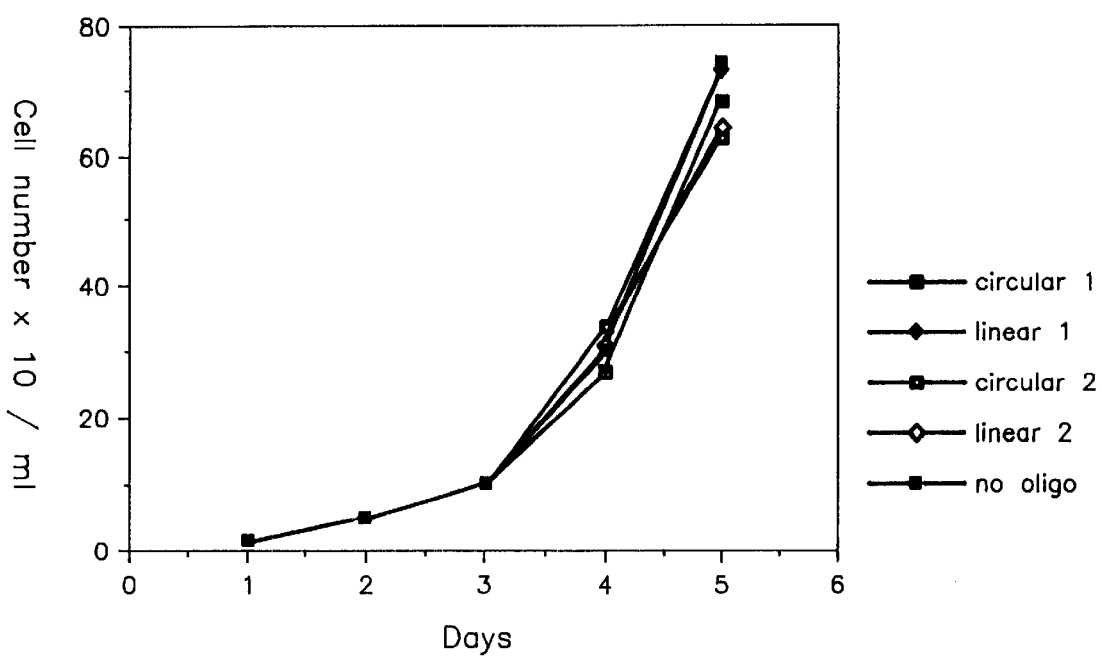

FIG. 9 shows the results of measurement of cell growth (Vero cells) in the presence of various linear or circular oligonucleotides, in comparison with the normal growth of the cells alone. In this experiment, the oligonucleotides were used at a concentration of 20 µM.

The results show that the growth curves are coincident. The linear or circular oligonucleotides do not appear to display any toxic effect on cell growth.

Analysis of the effects of circular oligonucleotides on the multiplication of HSV-1

Figure 10:
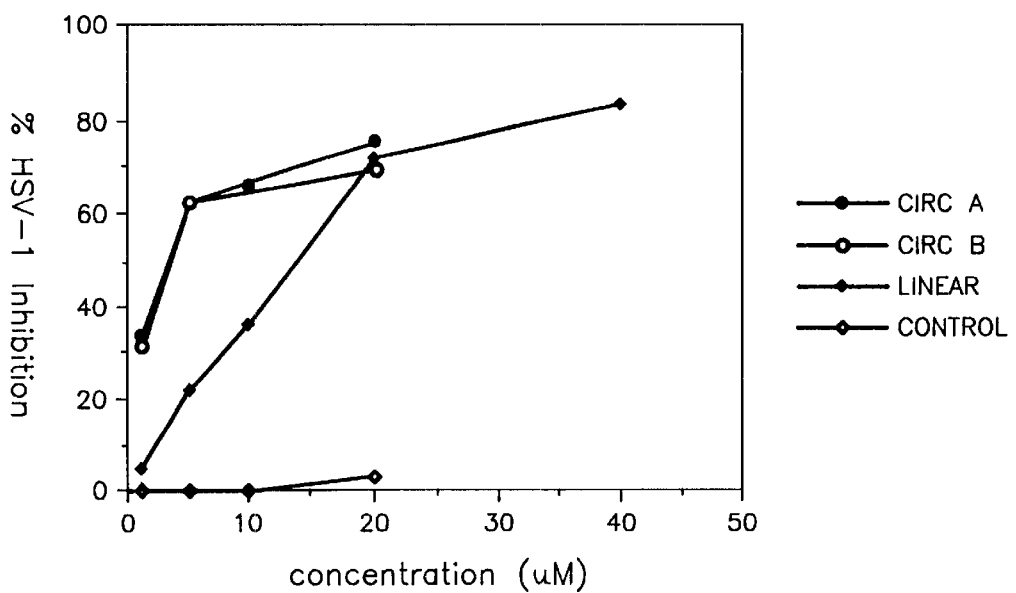

In this experiment, the effects of antisense oligonucleotides GT (the sequence of which is given above) in linear form or in circular form were compared. Two different inhibition conditions were compared. In A, the antisense nucleotides are added at the time of infection, whereas in B they are introduced into the medium 4 hours before infection. The results shown in FIG. 10 show that circular antisense oligonucleotides inhibit viral multiplication. The inhibition is 30% at 2 μM and reaches 65% at 5 μM. At these low concentrations, the circular oligonucleotides display an inhibitory effect which is greater than that of the linear oligonucleotide.

EXAMPLE 7

Properties of the "Sense" Type Oligonucleotides

1-Production of the Sense Type Oligonucleotides

Figure 1A:
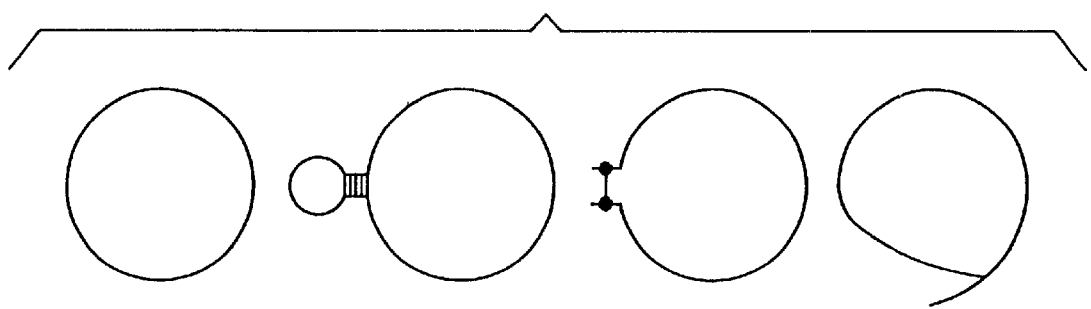
FIG. 1:
A—Examples of closed antisense oligonucleotide structures.
B—Examples of closed sense oligonucleotide structures.
C—Mixed molecule capable of exerting a sense and antisense effect.
D—Structure of the bases of which the oligonucleotides are composed and structure of the phosphodiester bond linking the natural nucleotides with one another.
Figure 1B:
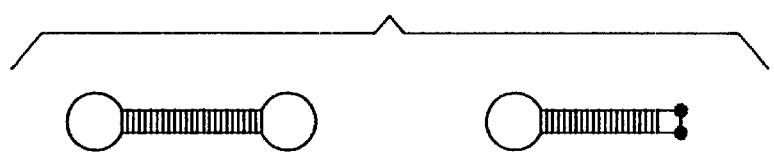
Figure 1C:
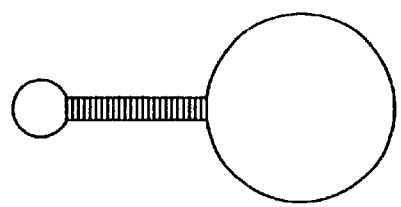
Figure 1D:
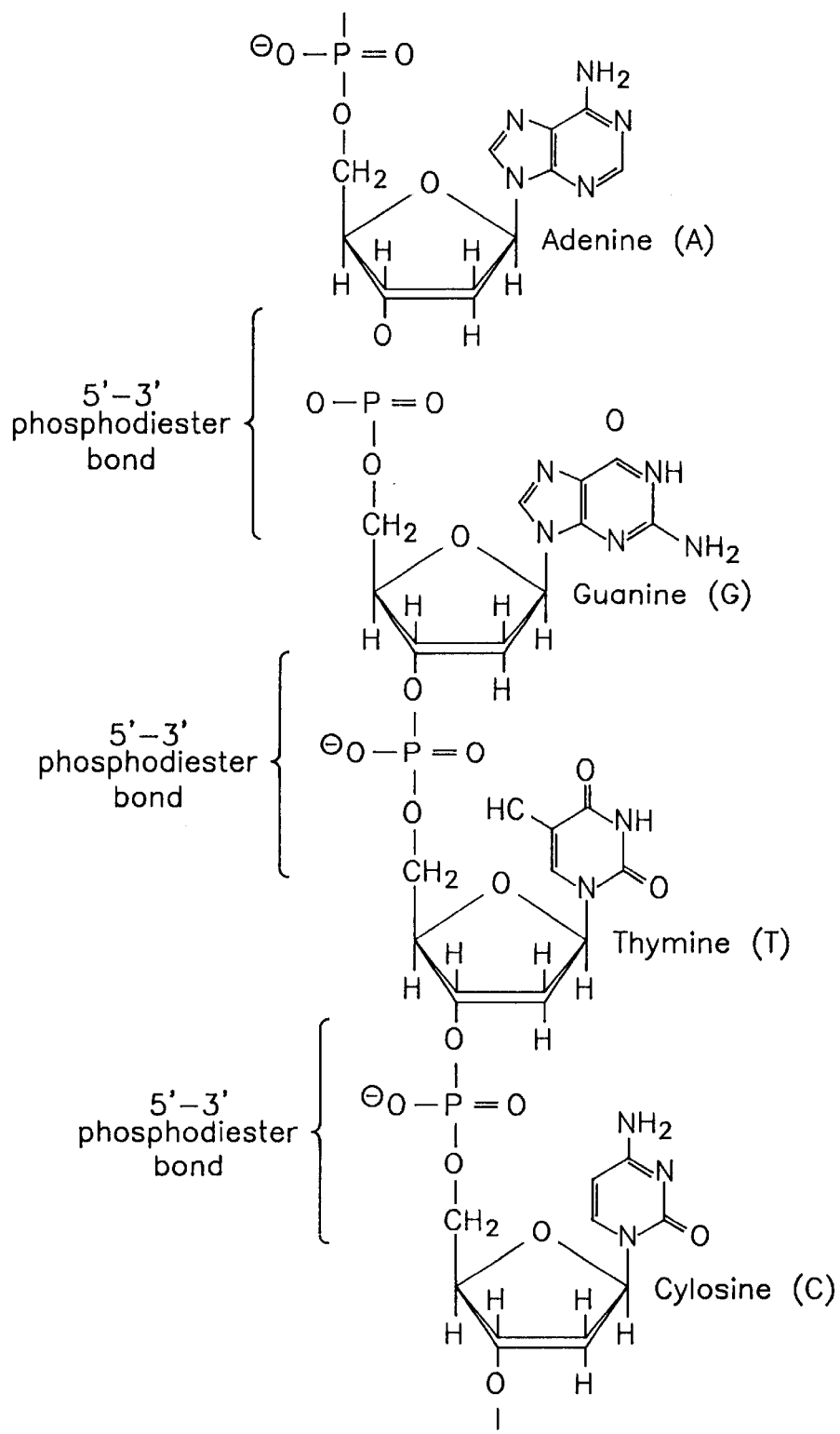
Figure 2A:
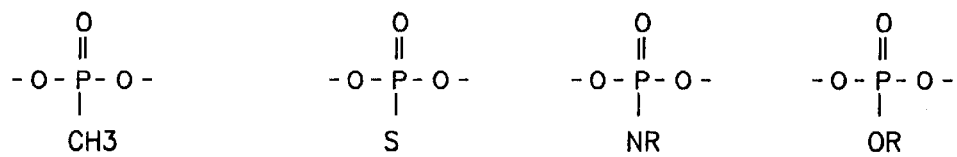
FIG. 2:
A—Diagrammatic representation of some of the modifications which can be used to increase the stability of the phosphodiester bond, and especially its endonuclease resistance.
B—Representation of a few intercalating type reactive agents which can be coupled to the antisense oligonucleotides.
Figure 2B:
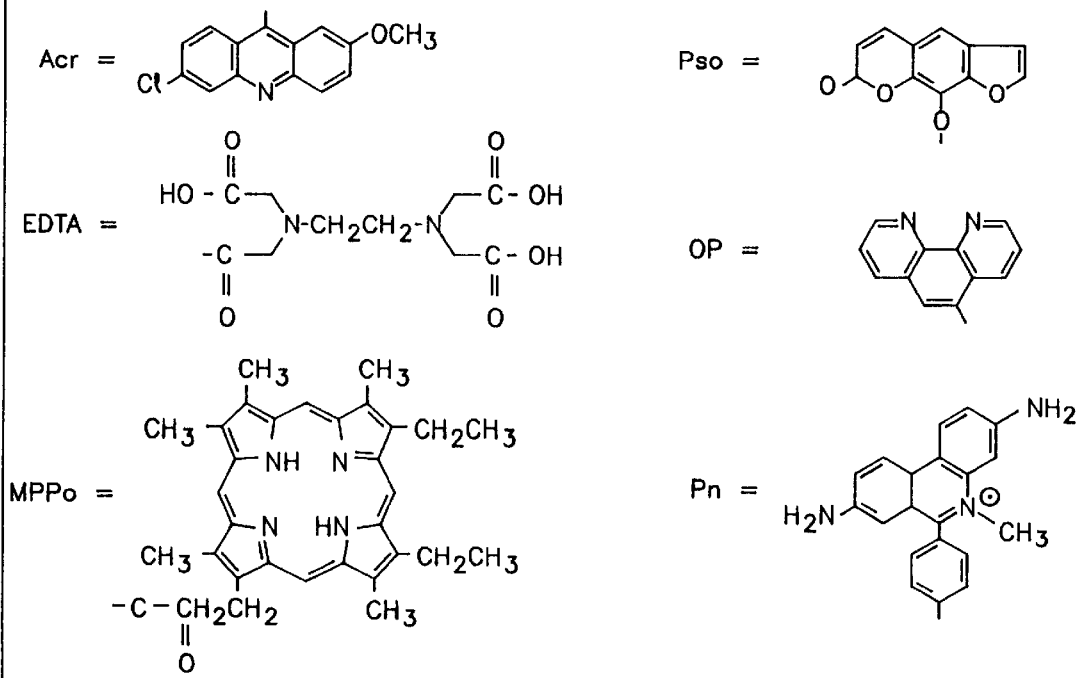
Figure 3:
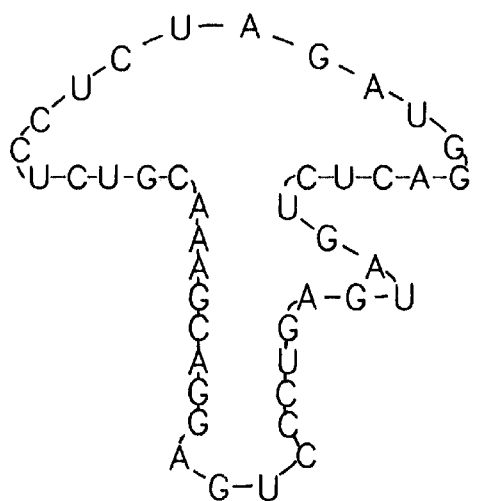
FIG. 3:
Example of a circular ribozyme containing the so-called "T-shaped" catalytic site and an RNA loop which can be complementary to a target sequence SEQ ID NO. 4.
Figure 4A:
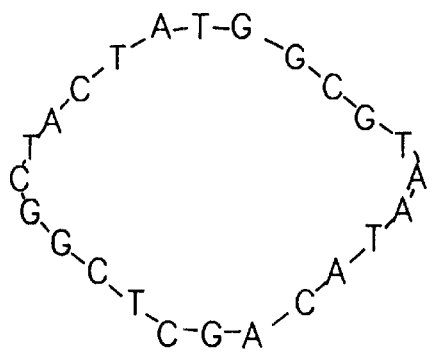
FIG. 4:
A—Diagrammatic representation of a circular oligonucleotide composed of natural nucleotides linked to one another via unmodified phosphodiester bonds SEQ ID NO. 5.
B—Diagrammatic representation of a lasso-shaped closed nucleotide with free 5' end and 3' end blocked in intra-chain bridging.
C—Diagrammatic representation of a balloon-shaped closed oligonucleotide with an intra-chain bond established between the penultimate 5' and 3' terminal nucleotides. This type of structure can contain one or more inter-chain bonds between any one of the pairs of paired nucleotides forming the tail of the balloon SEQ ID NO. 6.
D—Diagrammatic representation of an oligonucleotide closed with a peptide (oligopeptide).
E—Diagrammatic representation of a circular oligonucleotide containing a lateral peptide extension.
Figure 4B:
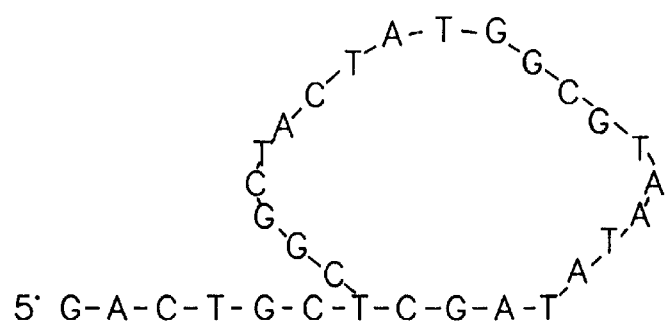
Figure 4C:
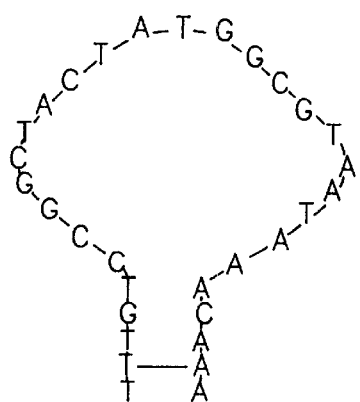
Figure 4D:
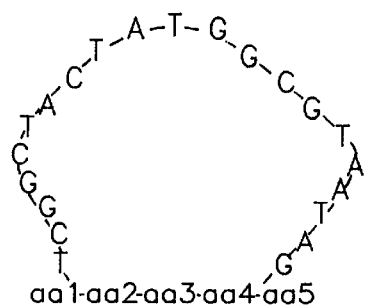
Figure 4E:
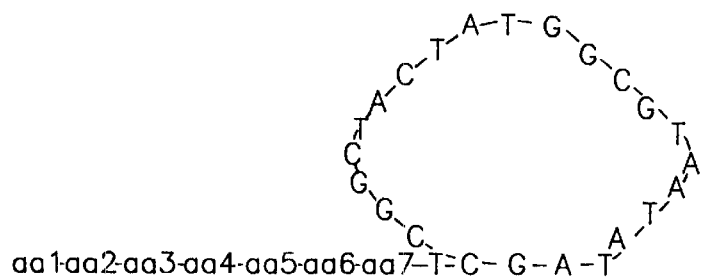
Figure 5A:
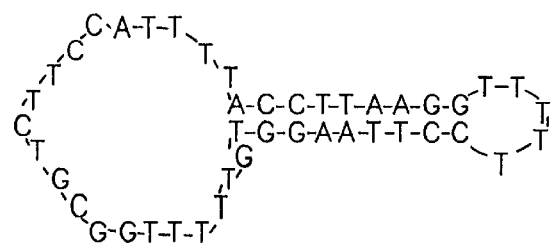
FIG. 5:
A—Diagrammatic representation of a circular, closed oligonucleotide containing a partial self-paired double-stranded region SEQ ID NO. 7.
B—Diagrammatic representation of a circular, closed oligonucleotide composed of a long self-paired double-stranded sequence (sequence for recognition of a transcription factor, for example) and two poly(T) joining loops (SEQ ID NO. 2).
Figure 5B:
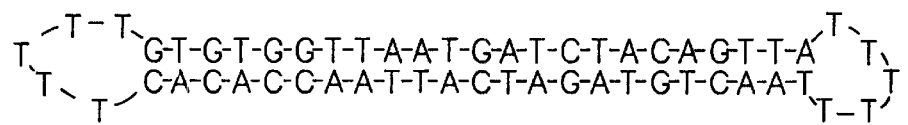

The experimental conditions permitting effective ligation of the oligonucleotide whose sequence is given in FIG. 5-B are similar to those described in Example 1.

The ligation products are then analyzed by denaturing electrophoresis on 12% polyacrylamide gel/7M urea.

serum. The comparisons performed between the resistance of the circularized oligonucleotides and that of the linear double-stranded oligonucleotides give the same results as those shown in FIG. 7-C. In all cases, the closed oligonucleotides display greater resistance than that of the non-closed oligonucleotides. The half-life of the closed sense oligonucleotides is greater than that of the non-closed, double-stranded linear oligonucleotides possessing free 3' and 5' ends by a factor of at least 10.

3-Demonstration of the binding of the transcription factor HNF-1 by a circular sense type oligonucleotide containing the recognition sequence in self-paired form.

The following experiments were carried out with the oligonucleotides whose sequence appears below:

HNF-1 UNLIGATED:

(SEQ ID NO.1)

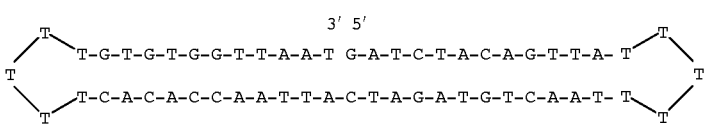

HNF1-CIRCULAR (HNF1-Cr):

(SEQ ID NO.2)

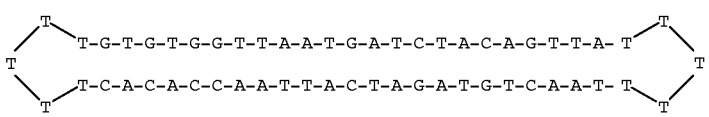

For the preparation of the labeled closed sense oligonucleotides used for the retarding gel experiments, the conditions are as follows:

22 nmol of oligonucleotide are labeled at the 5' end with gamma-32 [sic] ATP (specific activity 2–5×10⁸ cpm/μg), 50 mM Tris HCl pH 7.8, 10 mM MgCl2 [sic], 20 mM DTT, 1 mM ATP, 1 mM bSA [sic] and 400 units of T4 DNA ligase in a volume of 10 μl. Incubation takes place for 2 h at 16° C. The ligation products are purified by denaturing electrophoresis on 12% polyacrylamide gel/7M urea, the bands corresponding to the closed oligonucleotide are detected by autoradiography, excised from the gel, and the DNA is isolated by conventional techniques of extraction of polyacrylamide gels.

Alternatively, the products of the ligation reaction are used without prior purification, after inactivation of the DNA ligase by heating the ligation medium for 2 minutes at 90° C., extraction with phenol/chloroform/isoamil [sic] alcohol, precipitation with absolute alcohol in the presence of 20 μg of glycogen as entraining agent and washing with 80% alcohol.

2-Resistance of the Sense Type Oligonucleotides to Serum Nucleases

"Sense" oligonucleotides display resistance to nucleolytic degradation when they are incubated in the presence of HNFI-DOUBLE-STRANDED LINEAR (HNF1-DSL):
 -G-T-G-T-G-G-T-T-A-A-T-G-A-T-C-T-A-C-A-G-T-T-A-
 C-A-C-A-C-C-A-A-T-T-A-C-T-A-G-A-T-G-T-C-A-A-
 T-(SEQ ID NO. 2)

We compared the efficacy of binding of the transcription factor HNF1 (obtained from liver nuclear extracts) to double-stranded linear oligonucleotides, hairpin oligonucleotides and circular oligonucleotides, unligated or reclosed through the action of T4 ligase (sequence of the circular oligonucleotide used is given in FIG. 5-B).

Figure 11:
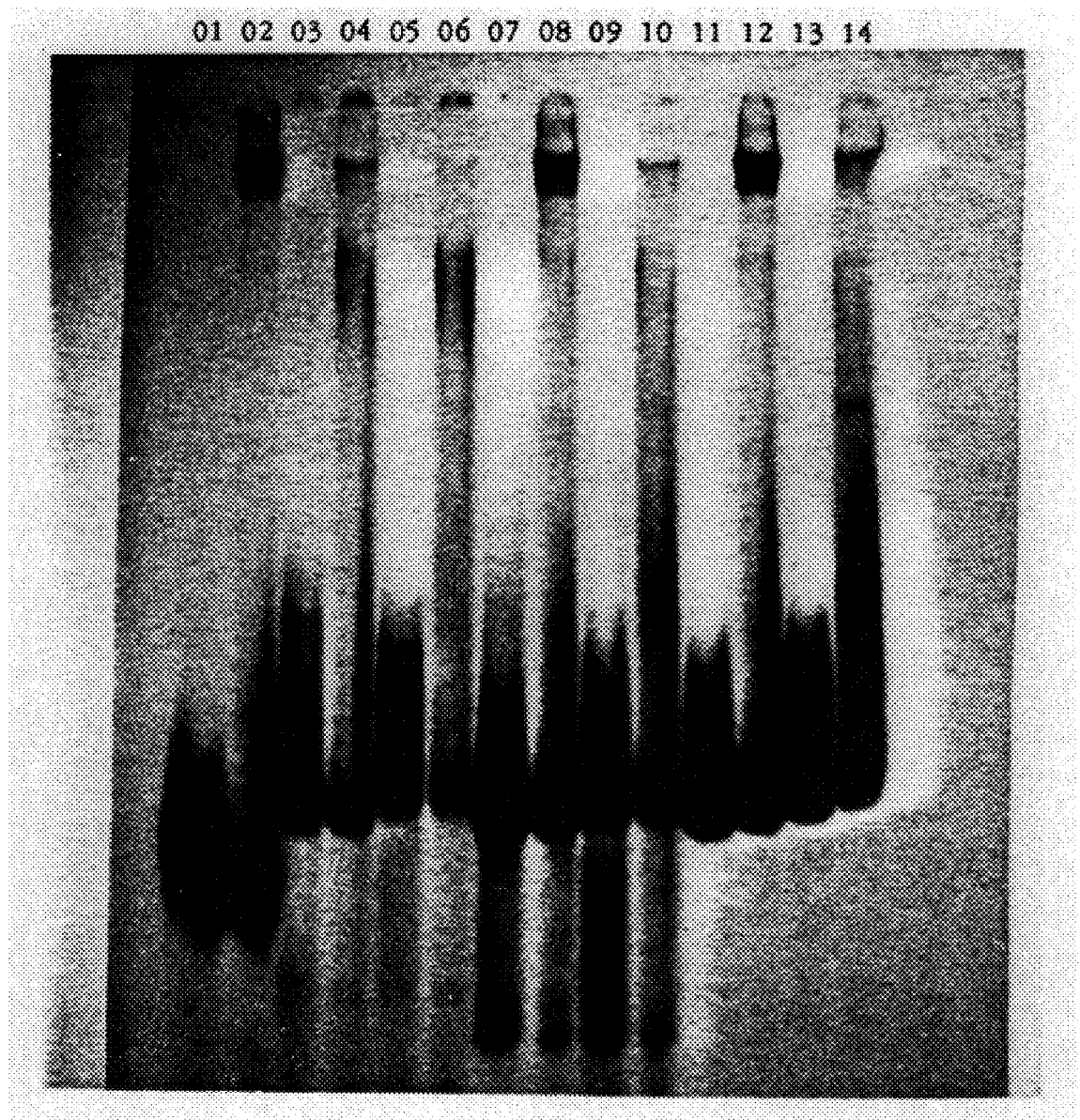

3 fmol of each oligonucleotide (specific activity 7000 cpm/fmol for the double-stranded linear oligonucleotide and 3500 cpm/fmol for the other oligonucleotides) are incubated in a final volume of 14 μl with 1 μg of a liver nuclear protein extract in 10 mM Hepes pH 7.9, 50 mM KDl, 10% glycerol, 0.1 mM EDTA, 0.5 mM DTT, 0.5 mM PMSF, 6 mM MgCl2 [sic], 6 mM spermine in the presence of 1.5 μg of poly (dI.dC)-poly(dI.dC) and 250 ng of sonicated salmon sperm DNA as non-specific competitors. After 10 min at 4° C., the reaction mixtures, together with controls in which the addition of proteins has been omitted, are spotted on a native 6% polyacrylamide gel/0.25×TBE. When migration is complete, the gel is fixed in 10% acetic acid, 10% metanol [sic] solution, transferred onto 3MM paper, dried and autoradiographed. The result of this experiment is shown in FIG. 11.

It is observed that:
1. The binding affinity of the transcription factor for the closed, circular oligonucleotide is similar to the binding observed on the double-stranded linear oligonucleotides (or hairpin oligonucleotides, results not shown here). Such structures may hence be used as an agent for binding transcription factors, trans-activators or all other proteins that bind to a specific DNA sequence.
2. The binding of the transcription factor HNF1 to the unligated circular oligonucleotide is 5- to 10-fold lower than that observed with the oligonucleotide circularized by ligase action. The ligation site in the sense pligonucleotide is centered in the double-stranded portion, and corresponds to the axis of the pseudopalindrome which constitutes the binding site of the dimer of HNF1. The presence of a "nick" hence destabilizes the DNA/protein binding. This result confirms the closed nature of the "sense" circular oligonucleotide treated with T4 ligase.

BIBLIOGRAPHIC REFERENCES CITED IN THE TEXT

Andrus, A.; Geiser, T.; Zon, G. (1989), *Nucleosides Nucleotides*, 8, 5–6, 967–8

Anfossi, Giovanni; Gewirtz, Alan M.; Calabretta, Bruno, (1989), *Proc. Natl. Acad. Sci. U.S.A.*, 86, 3379–83

Barbato, S., De Napoli, L., Mayol, L., Piccialli, G, and Santacroce, C. (1989). *Tetrahedron*, 54, 4523–4536

Bazile D; Gautier C; Rayner B; Imbach J L; Paoletti C; Paoletti J, (1989), *Nucleic Acids Res*, 17, 7749–59

Bertrand J R; Imbach J L; Paoletti C; Malvy C, (1989), *Biochem Biophys Res Commun*, 164, 311–8

Cameron F H; Jennings P A, (1989), *Proc Natl Acad Sci U S A*, 86, 9139–43

Caruthers, M. H. (1985) *Sciences*, 230, 281

Cazenave C; Chevrier M; Nguyen T T; Helene C, (1987), *Nucleic Acids Res*, 15, 10507–10521

Cazenave, C.; Stein, C. A.; Loreau, N.; Thuong, N. T.; Neckers, L. M.; Subasinghe, C.; Helene, C.; Cohen, J. S.; Toulme J. S., (1989), *Nucleic Acids Res*, 17, 4255–73

Chang, E. H.; Yu, Z.; Shinozuka, K.; Zon, G.; Wilson, W. D.; Strekowska, A., (1989), *Anti-Cancer Drug Des.*, 4, 221–32

Cope, F. O.; Wille, J. J., (1989), *Proc. Natl. Acad. Sci. U.S.A.*, 86, 5590–4

Cotton M. and Birnstiel M L. (1989). *EMBO J.* 8, 3861–3866

Cotten M; Schaffner G; Birnstiel M L, (1989), *Mol Cell Biol*, 9, 4479–87

Degols, G.; Leonetti, J. P.; Gagnor, C.; Lemaitre, M.; Lebleu, B.; (1989), *Nucleic Acids Res.*, 17, 9341–50

De Vroom E., Broxterman, H. J., Siedregt, L. A. J., Van der Marel, G. A., Van Broom, J. H., *Nucl. Ac. Res.*, 16, 4607–4620

Dervan PB, (1986), *Science*, 232, 464–71

Durand M; Maurizot J C; Asseline U; Barbier C; Thuong N T; Helene C, (1989), *Nucleic Acids Res*, 17, 1823–1837

Fedor M J; Uhlenbeck OC, (1990), *Proc Natl Acad Sci*, 87, 1668–72

Francois J C; Saison-Behmoaras T; Barbier C; Chassignol M; Thuong N T; Helene C, (1989), *Proc Natl Acad Sci*, 86, 9702–9706

Francois J C; Saison-Behmoaras T; Chassignol M; Thuong N T; Helene C, (1989), *J Biol Chem*, 264 5891–5898

Francois J C; Saison-Behmoaras T; Helene C, (1988), *Nucleic Acids Res*, 16, 11431–11440

Francois J C; Saison-Behmoaras T; Thuong N T; Helene C, (1989), *Biochemistry*, 28, 9617–9619

Froehler, B. C., Ng, P and Matteucci, M. D. (1986) *Nucl. Acid Res.*, 14, 5399

Gagnor, C., Bertrand, J. R., Thenet, S., Lemaitre, M., Morvan, F., Rayner, B., Malvy, C., Lebleu, B., Imbach, J. L., Paoletti, C., (1987), *Nucleic Acids Res*, 15, 10419–36

Gao, W., Stein, C. A., Cohen, J. S., Dutchmann, G. and Cheng, Y. C., (1988). *J. Biol. Chem.*, 264 11521–11532

Goodchild, John; Agrawal, Sudhir; Civeira, Maria P.; Sarin, Prem S.; Sun, Daisy; Zamecnik, Paul C., (1988), *Proc. Natl. Acad. Sci. U.S.A.*, 85, 5507–11

Haseloff J; Gerlach W L, (1988), *Nature*, 334, 585–91

Helene C, (1989) *Br J Cancer*, 60, 157–60

Helene C; Thuong N T, (1988), *Biochem Pharmacol*, 37, 1797–1798

Jeffries A C; Symons R H, (1989), *Nucleic Acids Res*, 17, 1371–7

Jessus C; Chevrier M; Ozon R; Helene C; Cazenave C, (1989), *Gene*, 72, 311–312

Kabanov, A. V.; Vinogradov, S. V.; Ovcharenko, A. V.; Krivonos, A. V.; Melik-Nubarov, N. S.; Kiselev, V. I.; Severin, E. S., (1990), *FEBS Lett.*, 259, 327–30

Le Doan T; Chavany C; Helene C, (1989) *Bull Cancer*, 76, 849–52

Leonetti, J. P., Degols, G., Milhaud, P., Gagnor, C., Lemaitre, M., Lebleu, B., (1989), *Nucleosides Nucleotides*, 8, 5–6, 825–8

Maher, Louis J, III; Dolnick, Bruce J., (1988), *Nucleic Acids Res.*, 16, 3341–58

Marcus-Sekura, Carol J.; Woerner, Amy M.; Shinozuka, Kazuo; Zon, Gerald; Quinnan, Gerald V., Jr., (1987), *Nucleic Acids Res.*, 15, 5749–63

Matsukura, Makoto; Zon, Gerald; Shinozuka, Kazuo; Robert-Guroff, Marjorie; Shimada, Takashi; Stein, C. A.; Mitsuya, Hiroaki; Mitsuya, Hiroaki; Wong-Staal, Flossie; et al., (1989), *Proc. Natl. Acad. Sci. U.S.A.*, 86, 4244–8

Miroschnichenko, O. I.; Ponomareva, T. I.; Tikhonenko, T. I., (1989), *Gene*, 84, 83–9

Perbost M; Lucas M; Chavis C; Pompon A; Baumgartner H; Rayner B; Griengl H; Imbach J L, (1989), *Biochem Biophys Res Commun*, 165, 742–7

Perroualt, L., Asseline, U., Rivalle, C., Thuong, N. Y., Bisagni, E., Giovanelli, C., LeDoan, T. and Helene, C. (1990). *Nature*, 344, 358–361

Sampson, J. R.; Sullivan, F. X.; Behlen, L. S.; DiRenzo, A. B.; Uhlenbeck, O. C., (1987), *Cold Spring Harbor Symp. Quant. Biol.*, 52, 267–75

Sankar, Sabita; Cheah, Keat Chye; Porter, Alan. G., (1989), *Eur. J. Biochem.*, 39–45

Sarver, N., Cantin, E. M., Pairoj, S. C., Zaia, J. A., Ladne, P. A., Stephens, D. A. and Rossi, J. J. (1990). *Science*, 247, 1222–1225.

Sheldon C C; Symons R H, (1989), *Nucleic Acids Res*, 17, 5679–85

Sheldon C C; Symons R H, (1989), *Nucleic Acids Res*, 17, 5665–77

Shuttleworth, John; Matthews, Glenn; Dale, Les; Baker, Chris; Colman, Alan, (1988), Gene, 72, 1–2, 267–75

Stevenson, Mario; Iversen, Patrick L., (1989), *J. Gen. Virol.*, 70, 2673–82

Sun J S; Asseline U; Rouzaud D; Montenay-Gerestier T; Nguyen T T; Helene C, (1987), *Nucleic Acids Res*, 15, 6149–69

Sun J S; Francois J C; Lavery R; Saison-Behmoaras T; Montenay-Gerestier T; Thuog N T; Helene C, (1988), *Biochemistry*, 27, 6039–6045

Sun J S; Francois J C; Montenay-Gerestier T; Saison-Behmoaras T; Roig V; Thuong N T; Helene C, (1989), *Proc Natl Acad Sci* 86, 9198–9202

Symons R H, (1989), *Trends Biochem Sci*, 14, 445–50

Symons R H; Hutchins C H; Forster A C; Rathjen P D; Keese P; Visvader J E, (1987), *J Cell Sci Suppl*, 7, 303–18

Tortora, Giampaolo; Clair, Timothy; Cho-Chung, Yoon Sang, (1990), *Proc. Natl. Acad. Sci. U.S.A.*, 87, 705–8

Toulme J J; Krisch H M; Loreau N; Thuong N T; Helene C, (1986), *Proc Natl Acad Sci*, 83, 1227–31

Trung Le Doan; Perrouault L; Chassignol M; Nguyen T T; Helene C, (1987), *Nucleic Acid Res*, 15, 8643–8659

Uhlenbeck, Olke C., (1987), *Nature*, 328, 596–600

Uhlenbeck, Olke C.; Dahm, Sue Ann C.; Ruffner, Duane E.; Fedor, Martha J., (1989), *Nucleic Acids Symp. Ser.*, 21, 95–6

Vasseur, M. (1990), *Biofutur*, April 1990, 18–28.

Verspieren P; Cornelissen A W; Thuong N T; Helene C; Toulme J J, (1987), *Gene*, 61, 307–315

Vlassov, V. V., Zarytova, V. F., Kutiavin, I. V., Mamaev, S. V. and Podyminogin, M. A. (1986) *Nucl. Acids Res.*, 14, 4065–4076.

Wang A H; Cottens S; Dervan P B; Yesinowski J P; van der Marel G A; van Boom J H, (1989), *J Biomol Struct Dyn*, 7, 101–17

Westermann, P.; Gross, B.; Hoinkis, G.; (1989), *Biomed. Biochim. Acta*, 48, 85–93

Zerial A; Thuong N T; Helene C, (1987), *Nucleic Acids Res*, 15, 9909–9919

Zheng, H., Sahai, Beni M., Kilgannon, P., Fotedar, A., Green, D. R., (1989), *Proc. Natl. Acad. Sci. U.S.A.*, 86, 3758–62

What is claimed is:

1. An antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed, single-stranded branched structure wherein the nucleotide sequence does not contain sequences capable of self-pairing.

2. The antisense or sense agent as claimed in claim 1, wherein the single-stranded oligonucleotide sequence is a sequence whose 5' and 3' ends are linked via a non-nucleoside monophosphate linkage as a covalent part of the backbone.

3. The antisense or sense agent as claimed in claim 2, wherein a compound is coupled to the non-nucleoside monophosphate linkage, where the compound is a bridging agent, an intercalating agent, or a cleaving agent or a molecule increasing intracellular penetration.

4. The antisense or sense agent as claimed in claim 3, wherein the, non-nucleoside monophosphate linkage is a peptide.

5. The antisense or sense agent as claimed in claim 3, wherein the non-nucleoside monophosphate linkage is a lipid.

6. A method of using the agent as claimed in claim 2, as an antiviral or anticancer agent or as an inducer of natural immuno-modulators, comprising administering to a patient in need thereof a therapeutically effective amount of the agent.

7. A method of using the agent of claim 2 in the treatment of dermatological pathology comprising topically administering to a patient in need thereof a pharmaceutically effective amount of the agent.

8. The antisense or sense agent as claimed in claimed 1, wherein the single-stranded oligonucleotide sequence is a sequence whose 5' and 3' ends are linked to one another via a phosphodiester internucleotide bond.

9. A method of using the agent as claimed in claim 8, as an antiviral or anticancer agent or as an inducer of natural immuno-modulators, comprising administering to a patient in need thereof a therapeutically effective amount of the agent.

10. A method of using the agent of claim 8 in the treatment of dermatological pathology comprising topically administering to a patient in need thereof a pharmaceutically effective amount of the agent.

11. The antisense or sense agent as claimed in claim 1, wherein the single-stranded oligonucleotide sequence is a sequence whose ends are covalently linked.

12. The antisense or sense agent as claimed in claim 1, wherein the nucleotide sequence contains sequences capable of pairing to form double-stranded self-pairings.

13. The antisense or sense agent as claimed in claim 12, wherein the sequences capable of pairing are separated by sequences incapable of pairing.

14. The antisense or sense agent as claimed in claim 12, wherein the single-stranded oligonucleotide sequence comprises a sequence that can affinity-bind a protein.

15. The antisense or sense agent as claimed in claim 1, wherein a compound is coupled to the single-stranded oligonucleotide, wherein the compound is a bridging agent, an intercalating agent, or a cleaving agent of molecular increasing intracellular penetration.

16. The antisense or sense agent as claimed in claim 1, wherein the single-stranded sequence is a sequence complementary to a region of a messenger RNA or of a natural DNA fragment.

17. The antisense or sense agent as claimed in claime 1, wherein the single-stranded oligonucleotide sequence comprises a sequence that can affinity-bind a protein.

18. The antisense or sense agent as claimed in claim 1, which contains a polyribonucleotide portion capable of exerting a trans cleavage activity on an RNA.

19. The antisense or sense agent as claimed in claim 1, wherein the oligonucleotide sequence contains between 10 and 100 nucleotides.

20. The antisense or sense agent as claimed in claim 19, wherein the oligonucleotide sequence contains between 20 and 50 nucleotide.

21. The method for preparing an agent as claimed in claim 1, wherein the partial or total chemical synthesis of the single-stranded chain of the compound has been performed before the latter is cvilized.

22. A method of using the agent as claimed in claim 1, as an antiviral or anticancer agent or as an inducer of natural immuno-modulators, comprising administering to a patient in need thereof a therapeutically effective amount of the agent.

23. A method as claimed in claim 22, wherein the agent is an interferon inducer.

24. A method of using the agent of claim 1 in the treatment of dermatological pathology comprising topically administering to a patient in need thereof a pharmaceutically effective amount of the agent.

25. In a method of in vitro diagnosis using an oligonucleotide agent, the improvement wherein the agent is the agent of claim 1.

26. A pharmaceutical composition comprising a pharmaceutically effective amount of the agent of claim 1 and a pharmaceutically acceptable carrier.

27. The composition as claimed in claim 26 in a form suitable for external topical administration.

28. In a cosmetic including a therapeutic agent, the improvement wherein the agent is the agent of claim 1.

29. The antisense or sense agent as claimed in claim 1, wherein the single-stranded oligonucleotide sequence comprises a sequence that can affinity-bind a protein.

30. An antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure wherein the single-stranded oligonucleotide sequence is a sequence whose 5' and 3' ends are linked via a non-nucleoside monophosphate linkage as a covalent part of the backbone and a compound selected from the group consisting of a bridging agent, an intercalating agent, a cleaving agent, and a molecule increasing intracellular penetration compound is coupled to the non-nucleoside monophosphate linkage and the non-nucleoside monophosphate linkage is a peptide or lipid linkage.

31. The antisense or sense agent of claim 30, wherein said linkage is a peptide linkage.

32. The antisense or sense agent of claim 30, wherein said linkage is a lipid linkage.

33. The antisense or sense agent of claim 30, wherein said compound is a bridging agent.

34. The antisense or sense agent of claim 30, wherein said compound is an intercalating agent.

35. The antisense or sense agent of claim 30, wherein said compound is a cleaving agent.

36. The antisense or sense agent of claim 30, wherein said compound is a molecule increasing intracellular penetration.

37. The antisense or sense agent as claimed in claim 30, wherein the single-stranded oligonucleotide sequence is a sequence whose 5' and 3' ends are linked via a non-nucleoside monophosphate linkage as a covalent part of the backbone.

38. The antisense or sense agent as claimed in claim 30, wherein the single-stranded oligonucleotide sequence is a sequence whose 5' and 3' ends are linked to one another via a phosphodiester intemucleotide bond.

39. The antisense or sense agent as claimed in claim 30, wherein the single-stranded oligonucleotide sequence is a sequence whose ends are covalently linked.

40. The antisense or sense agent as claimed in claim 30, wherein the nucleotide sequence does not contain sequences capable of self-pairing.

41. The antisense or sense agent as claimed in claim 40, wherein the single-stranded oligonucleotide sequence comprises a sequence that can affinity-bind a protein.

42. The antisense or sense agent as claimed in claim 30, wherein the nucleotide sequence contains sequences capable of pairing to form double-stranded self-pairings.

43. The antisense or sense agent as claimed in claim 42, wherein the fragments capable of pairing are separated by sequences incapable of pairing.

44. The antisense or sense agent as claimed in claim 42, wherein the single-stranded oligonucleotide sequence comprises a sequence that can affinity-bind a protein.

45. The antisense or sense agent as claimed in claim 30, wherein a compound is coupled to the single-stranded oligonucleotide, wherein the compound is a bridging agent, an intercalating agent, or a cleaving agent of molecular increasing intercellular penetration.

46. The antisense or sense agent as claimed in claim 30, wherein the single-stranded sequence is a sequence complementary to a region of a messenger RNA or of a natural DNA fragment.

47. The antisense or sense agent as claimed in claim 30, wherein the single-stranded oligonucleotide sequence comprises a sequence that can affinity-bind a protein.

48. The antisense or sense agent as claimed in claim 30, which contains a polyribonucleotide portion capable of exerting a trans cleavage activity on an RNA.

49. The antisense or sense agent as claimed in claim 30, wherein the oligonucleotide sequence contains between 10 and 100 nucleotides.

50. The antisense or sense agent as claimed in claim 30, wherein the oligonucleotide sequence contains between 20 and 50 nucleotides.

51. A method for preparing an agent as claimed in claim 30, wherein the partial or total chemical synthesis of the single-stranded chain of the compound has been performed before the latter is cyclized.

52. In a method of in vitro diagnosis using an oligonucleotide agent, the improvement wherein the agent is the agent of claim 30 and comprises contacting a biological sample with the agent of claim 30 in a hybridization assay.

53. A pharmaceutical composition comprising a pharmaceutically effective amount of the agent of claim 30 and a pharmaceutically acceptable carrier.

54. The composition as claimed in claim 53 in a form suitable for external topical administration.

55. In a cosmetic including a therapeutic agent, the improvement wherein the agent is the agent of claim 30.

56. A method of using an antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure wherein the single-stranded oligonucleotide sequence is a sequence whose 5' and 3' ends are linked via a non-nucleoside monophosphate linkage as a covalent part of the backbone and a compound selected from the group consisting of a bridging agent, an intercalating agent, a cleaving agent, and a molecule increasing intracellular penetration compound is coupled to the non-nucleoside monophosphate linkage and the non-nucleoside monophosphate linkage is a peptide or lipid linkage, as an antiviral or anticancer agent or as an inducer of natural immunomodulators, comprising administering to a patient in need thereof a therapeutically effective amount of the agent.

57. The method of claim 56, wherein the single-stranded oligonucleotide sequence is a sequence whose 5' and 3' ends are linked via a non-nucleoside monophosphate linkage as a covalent part of the backbone.

58. The method of claim 56, wherein the single-stranded oligonucleotide sequence is a sequence whose 5' and 3' ends are linked to one another via a phosphodiester internucleotide bond.

59. The method as claimed in claim 56, wherein the agent is an interferon inducer.

60. A method of using an antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure wherein the single-stranded oligonucleotide sequence is a sequence whose 5' and 3' ends are linked via a non-nucleoside monophosphate linkage as a covalent part of the backbone and a compound selected from the group consisting of a bridging agent, an intercalating agent, a cleaving agent, and a molecule increasing intracellular penetration compound is coupled to the non-nucleoside monophosphate linkage and the non-nucleoside monophosphate linkage is a peptide or lipid linkage, as an antiviral or anticancer agent or as an inducer of natural immunomodulators in the treatment of dermatological pathology comprising topically administering to a patient in need thereof a pharmaceutically effective amount of the agent.

61. The method of claim 60, wherein the single-stranded oligonucleotide sequence is a sequence whose 5' and 3' ends are linked via a non-nucleoside monophosphate linkage as a covalent part of the backbone.

62. The method of claim 60, wherein the single-stranded oligonucleotide sequence is a sequence whose 5' and 3' ends are linked to one another via a phosphodiester internucleotide bond.

63. An antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure and a polyribonucleotide portion capable of exerting a trans cleavage activity on an RNA.

64. The antisense or sense agent as claimed in claim 63, wherein the single-stranded oligonucleotide sequence is a sequence whose 5' and 3' ends are linked via a non-nucleoside monophosphate linkage as a covalent part of the backbone.

65. The antisense or sense agent as claimed in claim 64, wherein a compound is coupled to the single-stranded oligonucleotide, wherein the compound is a bridging agent, an intercalating agent, or a cleaving agent or a molecule increasing intracellular penetration.

66. The antisense or sense agent as claimed in claim 65, wherein the non-nucleoside monophosphate linkage is a peptide.

67. The antisense or sense agent as claimed in claim 65, wherein the non-nucleoside monophosphate linkage is a lipid.

68. The antisense or sense agent as claimed in claim 63, wherein the single-stranded oligonucleotide sequence is a sequence whose 5' and 3' ends are linked to one another via a phosphodiester internucleotide bond.

69. The antisense or sense agent as claimed in claim 63, wherein the single-stranded oligonucleotide sequence is a sequence whose ends are covalently linked.

70. The antisense or sense agent as claimed in claim 63, wherein the nucleotide sequence does not contain sequences capable of self-pairing.

71. The antisense or sense agent as claimed in claim 70, wherein the single-stranded oligonucleotide sequence comprises a sequence that can affinity-bind a protein.

72. The antisense or sense agent as claimed in claim 63, wherein the nucleotide sequence contains sequences capable of pairing to form double-stranded self-pairings.

73. The antisense or sense agent as claimed in claim 72, wherein the fragments capable of pairing are separated by sequences incapable of pairing.

74. The antisense or sense agent as claimed in claim 72, wherein the single-stranded oligonucleotide sequence comprises a sequence that can affinity-bind a protein.

75. The antisense or sense agent as claimed in claim 63, wherein a compound is coupled to the single-stranded oligonucleotide, wherein the compound is a bridging agent, an intercalating agent, or a cleaving agent, or a molecule increasing intracellular penetration.

76. The antisense or sense agent as claimed in claim 63, wherein the single-stranded sequence is a sequence complementary to a region of a messenger RNA or of a natural DNA fragment.

77. The antisense or sense agent as claimed in claim 63, wherein the single-stranded oligonucleotide sequence comprises a sequence that can affinity-bind a protein.

78. The antisense or sense agent as claimed in claim 63, wherein the oligonucleotide sequence contains between 10 and 100 nucleotides.

79. The antisense or sense agent as claimed in claim 78, wherein the oligonucleotide sequence contains between 20 and 50 nucleotides.

80. A method for preparing an agent as claimed in claim 63, wherein the partial or total chemical synthesis of the single-stranded chain of the compound has been performed before the latter is cyclized.

81. In a method of in vitro diagnosis using an oligonucleotide agent, the improvement wherein the agent is the agent of claim 63 and comprises contacting a biological sample with the agent of claim 63 in a hybridization assay.

82. A pharmaceutical composition comprising a pharmaceutically effective amount of the agent of claim 63 and a pharmaceutically acceptable carrier.

83. The composition of claim 82 in a form suitable for external topical administration.

84. In a cosmetic including a therapeutic agent, the improvement wherein the agent is the agent of claim 63.

85. A method of using an antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure and a polyribonucleotide portion capable of exerting a trans cleavage activity on an RNA, as an antiviral or anticancer agent or as an inducer of natural immuno-modulators, comprising administering to a patient in need thereof a therapeutically effective amount of the agent.

86. The method according to claim 85, wherein the single-stranded oligonucleotide sequence is a sequence whose 5' and 3' ends are linked via a non-nucleoside monophosphate linkage as a covalent part of the backbone.

87. The method of claim 85, wherein the single-stranded oligonucleotide sequence is a sequence whose 5' and 3' ends are linked to one another via a phosphodiester internucleotide bond.

88. The method of claim 85, wherein the agent is an interferon inducer.

89. A method of using an antisense or sense agent of the oligonucleotide type, comprising a single-stranded oligonucleotide sequence having a binding affinity for DNA, RNA, or protein selected from the group consisting of (a) a sequence whose ends are linked to one another via covalent linkage to form a closed, single-stranded structure, and (b) a sequence wherein one free end is linked to an internal nucleotide via covalent linkage to form a closed single-stranded branched structure and a polyribonucleotide portion capable of exerting a trans cleavage activity on an RNA in the treatment of dermatological pathology comprising topically administering to a patient in need thereof a pharmaceutically effective amount of the agent.

90. The method of claim 89, wherein the single-stranded oligonucleotide sequence is a sequence whose 5' and 3' ends are linked via a non-nucleoside monophosphate linkage as a covalent part of the backbone.

91. The method of claim 89, wherein the single-stranded oligonucleotide sequence is a sequence whose 5' and 3' ends are linked to one another via a phosphodiester internucleotide bond.

* * * * *

UNITED STATES PATENT AND TRADEMARK OFFICE
CERTIFICATE OF CORRECTION

PATENT NO.     : 6,369,038 B1
DATED          : April 9, 2002
INVENTOR(S)    : Marta Blumenfeld, Pascal Brandys, Luc d'Auriol and Marc Vasseur It is certified that error appears in the above-identified patent and that said Letters Patent is hereby corrected as shown below:

Column 3,
Line 43, "DNAS" should read -- DNAs --.

Column 6,
Line 10, "oligoribo nucleotides" should read -- oligoribonucleotides --.

Column 7,
Line 22, "3'-51" should read -- 3'-5' --.

Column 11,
Line 3, "oligo-nucleotides" should read -- oligonucleotides --.
Line 48, "phosphodiesterd" should read -- phosphodiesters --.
Line 57, "51 terminal" should read -- 5' terminal --.

Column 13,
Line 14, "$T_5$," should read -- $T_5$. --.

Column 18,
Line 23, "9 long strand." should read -- 9 (long strand). --.
Line 27, "9 long strand." should read -- 9 (long strand). --.
Line 35, "adn" should read -- and --.

Column 19,
Line 45, "synthesized urified" should read -- synthesized and purified --.
Line 57, "Si" should read -- S1 --.

Column 20,
Line 6, "ybridization" should read -- hybridization --.

Column 21,
Line 32, "10 MM" should read -- 10 mM --.

Column 23,
Line 18, "Malping" should read -- Mapping --.

Column 25,
Line 50, "5º C.CA" should read -- 5' CCA --.
Line 55, "5 0.25 M" should read -- 0.25 M --.
Line 56, "mM" should read -- 20 mM --.

UNITED STATES PATENT AND TRADEMARK OFFICE
CERTIFICATE OF CORRECTION

PATENT NO. : 6,369,038 B1
DATED : April 9, 2002
INVENTOR(S) : Marta Blumenfeld, Pascal Brandys, Luc d'Auriol and Marc Vasseur It is certified that error appears in the above-identified patent and that said Letters Patent is hereby corrected as shown below:

Column 26,
Line 26, "edium" should read -- medium --.

Column 28,
Line 45, "(SEQ ID NO. 2)" should read -- (SEQ ID NO. 3) --.
Line 56, "50 mM KDl" should read -- 50 mM KCl --

Column 29,
Lines 12-13, "pligonucleotide" should read -- oligonucleotide --.

Column 39,
Line 43, "claime" should read -- claim --.
Line 58, "cvilized" should read -- cyclized --.

Column 40,
Line 52, "intemucleotide" should read -- internucleotide --.

Column 42,
Lines 30-31, "intemucleotide" should read -- internucleotide --.

Column 44,
Lines 20-21, "intemucleotide" should read -- internucleotide --.

Signed and Sealed this

Fourth Day of February, 2003

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 56 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:1:

GATCTACAGT TATTTTTTAA CTGTAGATCA TTAACCACAC TTTTTGTGTG GTTAAT     56

(2) INFORMATION FOR SEQ ID NO:2:

(i) SEQUENCE CHARACTERISTICS:
      (A) LENGTH: 56 bases
      (B) TYPE: nucleic acid
      (C) STRANDEDNESS: single
      (D) TOPOLOGY: circular (ii) MOLECULE TYPE: DNA (genomic)

(iii) HYPOTHETICAL: NO (iv) ANTI-SENSE: YES (ix) FEATURE:
      (A) NAME/KEY: stem loop
      (B) LOCATION: 1..56
      (C) OTHER INFORMATION:

(xi) SEQUENCE DESCRIPTION: SEQ ID NO:2:

GATCTACAGT TATTTTTTAA CTGTAGATCA TTAACCACAC TTTTTGTGTG GTTAAT     56

(2) INFORMATION FOR SEQ ID NO:3:

(i) SEQUENCE CHARACTERISTICS:
      (A) LENGTH: 23 bases
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: misc feature
            (B) LOCATION: 1...23
            (C) OTHER INFORMATION:

(xi) SEQUENCE DESCRIPTION: SEQ ID NO:3:

GTGTGGTTAA TGATCTACAG TTA                                                      23

(2) INFORMATION FOR SEQ ID NO:4:

(i) SEQUENCE CHARACTERISTICS:
            (A) LENGTH: 42 bases
            (B) TYPE: nucleic acid
            (C) STRANDEDNESS: single
            (D) TOPOLOGY: circular (ii) MOLECULE TYPE: RNA (genomic)

(iii) HYPOTHETICAL: NO (iv) ANTI-SENSE: YES (ix) FEATURE:
            (A) NAME/KEY: stem loop
            (B) LOCATION: 1..42
            (C) OTHER INFORMATION:

(xi) SEQUENCE DESCRIPTION: SEQ ID NO:4:

AGGACGAAAC GUCUCCUCUA GAUGGACUCU GAUGAGUCCC UG                                  42

(2) INFORMATION FOR SEQ ID NO:5:

(i) SEQUENCE CHARACTERISTICS:
            (A) LENGTH: 24 bases
            (B) TYPE: nucleic acid
            (C) STRANDEDNESS: single
            (D) TOPOLOGY: circular (ii) MOLECULE TYPE: RNA (genomic)

(iii) HYPOTHETICAL: NO (iv) ANTI-SENSE: YES (ix) FEATURE:
            (A) NAME/KEY: stem loop
            (B) LOCATION:1..24
            (C) OTHER INFORMATION:

(xi) SEQUENCE DESCRIPTION: SEQ ID NO:5:

TGGCGTAATA CAGCTCGGCT ACTA                                                     24

(2) INFORMATION FOR SEQ ID NO:6:

(i) SEQUENCE CHARACTERISTICS:
            (A) LENGTH: 31 bases
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: YES (ix) FEATURE:
            (A) NAME/KEY: stem loop (B) LOCATION: 2..30
        (C) OTHER INFORMATION:

(xi) SEQUENCE DESCRIPTION: SEQ ID NO:6:

TTTGTCCGGC TACTATGGCG TAATAAACAA A                                      31

(2) INFORMATION FOR SEQ ID NO:7:

(i) SEQUENCE CHARACTERISTICS:
        (A) LENGTH: 44 bases
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: YES (xi) SEQUENCE DESCRIPTION: SEQ ID NO:7:

TTCCATTTTA CCTTCTGCGG TTTTTGTGGA ATTCCTTTTT GGAA                         44

(2) INFORMATION FOR SEQ ID NO:8:

(i) SEQUENCE CHARACTERISTICS:
        (A) LENGTH: 13 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:8:

TACGACGAGG CAT                                                          13

(2) INFORMATION FOR SEQ ID NO:9:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:9:

GTCGTATCGG CTCGTACATA ATATGCCTC                                         29

(2) INFORMATION FOR SEQ ID NO:10:

(i) SEQUENCE CHARACTERISTICS:
        (A) LENGTH: 44 bases
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES

-continued (xi) SEQUENCE DESCRIPTION: SEQ ID NO:10:

TTCCATTTTA CCTTCTGCGG TTTTTGTGGA ATTCCTTTTT GGAA         44

(2) INFORMATION FOR SEQ ID NO:11:

(i) SEQUENCE CHARACTERISTICS:
      (A) LENGTH: 28 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:11:

AATGATCTAC AGTTATTTTT TAACTGTA         28

(2) INFORMATION FOR SEQ ID NO:12:

(i) SEQUENCE CHARACTERISTICS:
      (A) LENGTH: 28 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:12:

GATCATTAAC CACACTTTTT GTGTGGTT         28

(2) INFORMATION FOR SEQ ID NO:13:

(i) SEQUENCE CHARACTERISTICS:
      (A) LENGTH: 28 bases
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:13:

GTGGGACGTT CCTCCTGCGG GAAGCGGC         28